(12) United States Patent
Barrett et al.

(10) Patent No.: US 10,881,347 B2
(45) Date of Patent: Jan. 5, 2021

(54) CLOSED LOOP DIALYSIS TREATMENT USING ADAPTIVE ULTRAFILTRATION RATES

(71) Applicant: Fresenius Medical Care Holdings, Inc., Waltham, MA (US)

(72) Inventors: Louis L. Barrett, West Point, UT (US); Ken Chhi, Fremont, CA (US); David Yuds, Hudson, NH (US); Tom Merics, Antioch, CA (US); Joan Dowd, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 374 days.

(21) Appl. No.: 15/927,769

(22) Filed: Mar. 21, 2018

(65) Prior Publication Data
US 2019/0200921 A1    Jul. 4, 2019

Related U.S. Application Data

(60) Provisional application No. 62/612,037, filed on Dec. 29, 2017.

(51) Int. Cl.
*A61B 5/00* (2006.01)
*A61M 1/34* (2006.01)
(Continued)

(52) U.S. Cl.
CPC .......... *A61B 5/4836* (2013.01); *A61B 5/0295* (2013.01); *A61B 5/14535* (2013.01);
(Continued)

(58) Field of Classification Search
CPC . A61B 5/4836; A61B 5/0295; A61B 5/14535; A61B 5/6866; A61B 5/14542;
(Continued)

(56) References Cited

U.S. PATENT DOCUMENTS 5,401,238 A    3/1995   Pirazzoli
6,626,857 B1   9/2003   Ohta et al.
(Continued)

FOREIGN PATENT DOCUMENTS

DE    40 24 434 A1   2/1992
EP    1 117 449 A1   7/2001

OTHER PUBLICATIONS

Baldamus, *Contr. Nephrol*, 44, 212-222 (1985).
(Continued)

*Primary Examiner* — Philip R Wiest
(74) *Attorney, Agent, or Firm* — Leydig, Voit & Mayer, Ltd.

(57) ABSTRACT

A method of performing closed-loop dialysis treatment during hemodialysis is provided. The method involves determining an initial ultrafiltration rate and setting an ultrafiltration pump of a dialysis system to the determined ultrafiltration rate. A series of measurements and calculations are made to ensure that a rate of change of blood volume during treatment follows a specified profile. A threshold may be used to keep the rate of change of blood volume tracking the profile. Patient fluid dynamics may be measured in real-time and used to determine the ultrafiltration pump rate.

14 Claims, 14 Drawing Sheets

(51) Int. Cl.
*A61M 1/16* (2006.01)
*A61B 5/0295* (2006.01)
*A61B 5/145* (2006.01)

(52) U.S. Cl.
CPC ......... *A61B 5/6866* (2013.01); *A61M 1/1603* (2014.02); *A61M 1/3403* (2014.02); *A61B 5/14542* (2013.01)

(58) Field of Classification Search
CPC .............. A61M 1/1603; A61M 1/1605; A61M 1/1607; A61M 1/1609; A61M 1/1613; A61M 1/3403
See application file for complete search history.

(56) References Cited

U.S. PATENT DOCUMENTS

| | | | |
|---|---|---|---|
| 6,689,083 B1 | 2/2004 | Gelfand et al. | |
| 6,706,007 B2 | 3/2004 | Gelfand et al. | |
| 6,733,471 B1 | 5/2004 | Ericson et al. | |
| 6,939,471 B2 | 9/2005 | Gross et al. | |
| 6,966,979 B2 | 11/2005 | Pedrazzi | |
| 7,029,456 B2 | 4/2006 | Ware et al. | |
| 7,153,473 B2 | 12/2006 | Ericson et al. | |
| 7,175,809 B2 | 2/2007 | Gelfand et al. | |
| 7,648,475 B2 | 1/2010 | De Cicco et al. | |
| 7,731,689 B2 | 6/2010 | Prisco et al. | |
| 7,788,038 B2 | 8/2010 | Oshita et al. | |
| 7,857,976 B2 | 12/2010 | Bissler et al. | |
| 8,070,707 B2 | 12/2011 | Gelfand et al. | |
| 8,078,333 B2 | 12/2011 | Kienman et al. | |
| 8,105,260 B2 | 1/2012 | Tonelli et al. | |
| 8,480,609 B2 | 7/2013 | Fava et al. | |
| 8,647,290 B2 | 2/2014 | Masala et al. | |
| 8,992,463 B2 | 3/2015 | Hogard et al. | |
| 9,005,150 B2 | 4/2015 | Ware et al. | |
| 9,022,966 B2 | 5/2015 | Lannoy | |
| 9,039,647 B2 | 5/2015 | Lannoy | |
| 9,199,027 B2 | 12/2015 | Fontanazzi et al. | |
| 9,220,830 B2 | 12/2015 | Fontanazzi et al. | |
| 9,399,090 B2 | 7/2016 | Collier et al. | |
| 9,415,150 B2 | 8/2016 | Hogard et al. | |
| 9,486,568 B2 | 11/2016 | Atallah et al. | |
| 9,504,777 B2 | 11/2016 | Hogard et al. | |
| 9,533,087 B2 | 1/2017 | Suffritti et al. | |
| 9,545,469 B2 | 1/2017 | Curtis et al. | |
| 9,561,316 B2 | 2/2017 | Gerber et al. | |
| 9,572,919 B2 | 2/2017 | Kelly et al. | |
| 9,579,439 B2 | 2/2017 | Wolff | |
| 9,582,164 B2 | 2/2017 | Stenquist | |
| 9,585,992 B2 | 3/2017 | Bene | |
| 9,597,440 B2 | 3/2017 | Gerber et al. | |
| 9,610,393 B2 | 4/2017 | Rada et al. | |
| 9,610,394 B2 | 4/2017 | Cappella et al. | |
| 9,629,949 B2 | 4/2017 | Akonur et al. | |
| 9,642,960 B2 | 5/2017 | Gerber et al. | |
| 9,675,745 B2 | 6/2017 | Kelly et al. | |
| 9,750,865 B2 | 9/2017 | Vasta et al. | |
| 9,764,074 B1 | 9/2017 | Childers et al. | |
| 9,770,546 B2 | 9/2017 | Vasta | |
| 9,814,820 B2 | 11/2017 | Childers et al. | |
| 2002/0085951 A1* | 7/2002 | Gelfand ................ | A61M 1/34 422/44 |
| 2004/0057037 A1* | 3/2004 | Ohishi ................ | A61M 1/1613 356/39 |
| 2005/0043665 A1 | 2/2005 | Vinci et al. | |
| 2007/0108129 A1* | 5/2007 | Mori ..................... | A61M 1/361 210/646 |
| 2007/0175827 A1 | 8/2007 | Wariar | |
| 2010/0000944 A1 | 1/2010 | Paolini et al. | |
| 2011/0098625 A1 | 4/2011 | Masala et al. | |
| 2011/0218486 A1 | 9/2011 | Huitt et al. | |
| 2011/0264025 A1 | 10/2011 | Lannoy | |
| 2011/0288464 A1 | 11/2011 | Lannoy | |
| 2013/0190674 A1 | 7/2013 | Case et al. | |
| 2013/0226065 A1 | 8/2013 | Wolff et al. | |
| 2014/0074008 A1 | 3/2014 | Fontanazzi et al. | |
| 2014/0088483 A1 | 3/2014 | Fontanazzi et al. | |
| 2014/0217020 A1 | 8/2014 | Meyer et al. | |
| 2014/0217030 A1 | 8/2014 | Meyer et al. | |
| 2014/0296766 A1 | 10/2014 | Krause et al. | |
| 2015/0258263 A1 | 9/2015 | Hogard et al. | |
| 2015/0343129 A1 | 12/2015 | Surace et al. | |
| 2016/0022897 A1 | 1/2016 | Weigel et al. | |
| 2016/0331884 A1 | 11/2016 | Sigg et al. | |
| 2016/0354528 A1 | 12/2016 | Pouchoulin | |
| 2016/0361485 A1 | 12/2016 | Tonyi | |
| 2016/0367743 A1 | 12/2016 | Jansson | |
| 2016/0375189 A1 | 12/2016 | Rohde et al. | |
| 2016/0375190 A1 | 12/2016 | Blatter et al. | |
| 2017/0000938 A1 | 1/2017 | Wilt | |
| 2017/0014566 A1 | 1/2017 | Childers et al. | |
| 2017/0028120 A1 | 2/2017 | Kelly et al. | |
| 2017/0043078 A1 | 2/2017 | Thiebaud et al. | |
| 2017/0065760 A1 | 3/2017 | Suffritti et al. | |
| 2017/0065762 A1 | 3/2017 | Larsen et al. | |
| 2017/0095602 A1 | 4/2017 | Ishizaki et al. | |
| 2017/0095605 A1 | 4/2017 | Childers et al. | |
| 2017/0100529 A1 | 4/2017 | Gerber et al. | |
| 2017/0112989 A1 | 4/2017 | Grant et al. | |
| 2017/0143888 A1 | 5/2017 | Childers et al. | |
| 2017/0173253 A1 | 6/2017 | Funkhouser | |
| 2017/0182237 A1 | 6/2017 | Burbank et al. | |
| 2017/0203024 A1 | 7/2017 | Burbank et al. | |
| 2017/0203027 A1 | 7/2017 | Burbank et al. | |
| 2017/0232175 A1 | 8/2017 | Burbank et al. | |
| 2017/0239409 A1 | 8/2017 | De Los Reyes, V et al. | |
| 2017/0246368 A1 | 8/2017 | Giordano et al. | |
| 2017/0266360 A1 | 9/2017 | Burbank et al. | |
| 2017/0281845 A1 | 10/2017 | Manda et al. | |
| 2017/0281847 A1 | 10/2017 | Manda et al. | |
| 2017/0296726 A1 | 10/2017 | Riemenschneider | |
| 2017/0296727 A1 | 10/2017 | Burbank et al. | |
| 2017/0296736 A1 | 10/2017 | Golarits et al. | |
| 2017/0304516 A1 | 10/2017 | Burnes | |
| 2017/0312413 A1 | 11/2017 | Fujiwara et al. | |
| 2017/0312414 A1 | 11/2017 | Fujiwara et al. | |
| 2017/0319765 A1 | 11/2017 | Wilt et al. | |
| 2017/0319768 A1 | 11/2017 | Szpara et al. | |
| 2017/0319769 A1 | 11/2017 | Wieslander et al. | |
| 2017/0319770 A1 | 11/2017 | Fitzgerald et al. | |
| 2017/0319771 A1 | 11/2017 | Vasta et al. | |
| 2017/0326282 A1 | 11/2017 | Wilt et al. | |
| 2017/0368248 A1 | 12/2017 | Neftel et al. | |

OTHER PUBLICATIONS

Bosch et al., *High Flux Hemofiltration-Artificial Organs*, 2(4), 339-342 (Nov. 1978).
Deen et al., *J. Clin. Invest.*, 52, 1500-1508 (Jun. 1973).
Drukker, Parsons, Maher, *Replacement of Renal Function by Dialysis*, 41th ed., pp. 134-140, 215-216, 380-383, 390-412. Kluwer Academic Publishers, Dordrecht (1996).
Lauer et al., *Annals of Internal Med.*, 99, 455-460 (1983).
Mann et al., *Nephrol. Dial. Transplant*, 11, Suppl. 8, 10-15 (1996).
Nikkiso DBB-06® Hemodialysis System, Nikkiso America, Inc. (2016).
Nussbaumer et al., Sonderdruck aus "Wissenschaftliche Informationen," Fresenius, Nephrologie, 145-155 (1978).
International Patent Application No. PCT/US2018/067049, Search Report (Mar. 7, 2019).

\* cited by examiner

CLOSED LOOP DIALYSIS TREATMENT USING ADAPTIVE ULTRAFILTRATION RATES

CROSS-REFERENCE TO RELATED APPLICATIONS

This application claims the benefit of U.S. Provisional Application No. 62/612,037, filed on Dec. 29, 2017, which is hereby incorporated by reference in its entirety.

BACKGROUND

Patients with kidney failure or partial kidney failure typically undergo kidney dialysis, often at a hemodialysis treatment center. When healthy, kidneys maintain the body's internal equilibrium of water and minerals (e.g., sodium, potassium, chloride, calcium, phosphorous, magnesium, and sulfate). Patients with kidney failure tend to accumulate substantial excess water and toxins (e.g., urea, ammonia) in their blood and tissues and may experience serious mineral imbalances. The kidneys also function as part of the endocrine system to produce the hormone erythropoietin, as well as other hormones. Hemodialysis is an imperfect treatment to replace kidney function, in part, because it does not address the endocrine functions of the kidney.

In hemodialysis, blood is withdrawn from the patient through an intake needle (or catheter) which draws blood from an artery in a specific access site (e.g., arm, thigh, subclavian region, etc.). The arterial blood is then pumped through extracorporeal tubing typically via a peristaltic pump, and then through a special filter termed a "dialyzer." The dialyzer is designed to remove toxins such as urea, nitrogen, potassium, and excess water from the blood. As blood enters the dialyzer, it distributes into thousands of small-diameter, straw-like, generally-parallel fibers that run the length of the dialyzer. The walls of each fiber are formed from a semi-permeable membrane material with numerous small pores. Dialysate, a solution of chemicals and water, flows through the dialyzer in the spaces outside this network of fibers and generally in a direction opposite (i.e., counter-current with) the flow of the blood. As the dialysate flows through the dialyzer, it bathes and surrounds the fibers. These pores in fiber membranes are large enough to pass water and water-borne impurities—including minerals, urea and other small molecules—but are not large enough to pass red blood cells. Fresh dialysate thus accumulates excess impurities passing by diffusion across the membranes, and also collects excess water through an ultrafiltration (UF) process due to a hydrostatic pressure difference across the membrane (i.e., due to a higher hydrostatic pressure in the blood as compared to the dialysate).

During this process, the volume of the relatively-large cells and larger proteins in the blood remains within the fibers to be recirculated back to the body. Used dialysate exits the dialyzer with excess fluids and toxins via an output tube, thus cleansing the blood and red cell volume flowing through the dialyzer. The cleansed, dialyzed blood then flows out of the dialyzer via tubing and a needle (or catheter) back into the patient (e.g., into an adjacent vein at the same access site). Sometimes, a heparin drip or pump is provided along the extracorporeal blood flow loop to prevent red cell clotting during hemodialysis. By combining hemodialysis and ultrafiltration, several liters of excess fluid can be removed from the patient in a typical multi-hour treatment. In the U.S., a patient with chronic kidney failure will normally undergo hemodialysis treatment in a dialysis center three times per week, either on a Monday-Wednesday-Friday schedule or a Tuesday-Thursday-Saturday schedule. These treatments are typically completed over 3 to 4 hours, with blood flow rates through the dialyzer typically set relatively high at 300 ml/minute or more. Ultrafiltration rates in the U.S. typically range between 1 to 3 liters per hour, with periodic "shut-down" minimum periods approaching 0 liters/hr. In other countries, the flow rates and time for treatment are generally lower and longer, respectively. Lower blood flow rates or ultrafiltration rates require a longer treatment time to achieve the same level of clearance of toxins and water from the body.

Current methods of performing dialysis are based on estimates of the amount of fluid which can be removed from a patient based on the patient's weight at the time of arrival for regular treatments; their "target" weight as determined by accepted algorithms using factors such as height, weight and other physiological conditions; and the physicians orders for the treatments.

Kidney failure patients cannot remove excess fluid through normal excretion. Much of this excess fluid instead passes from the blood into the interstitial tissue space, including around muscle tissue. The process of dialysis is, in part, designed to remove fluids from the vascular space, encouraging fluid accumulated in the interstitial tissue to migrate back into the bloodstream by osmosis and hydrostatic effects. This natural process of fluid moving from the interstitial tissues and into the blood is termed "re-filling" and should be considered when evaluating the success of dialysis.

The challenge of dialysis is to remove sufficient fluid from the bloodstream that the body mechanics can re-fill the volume removed by treatment. If the dialysis process removes fluid too quickly, the blood volume will drop excessively because the body either cannot keep up through re-filling, or the patient will have no more stored fluid and nothing to "re-fill" with. This condition can result in a morbidity event resulting in cramps, nausea and a potentially more serious condition for the patient.

If insufficient fluid is removed from the blood stream by the dialysis process, then there will be no movement of fluid from the interstitial tissue to the vascular system and the treatment will be rather ineffective. A goal in dialysis is thus to find a balance where dialysis challenges the patient's vascular system volume sufficiently to remove unwanted interstitial fluid, while at the same time not contributing to patient morbidity.

SUMMARY

In an exemplary embodiment, the disclosure provides a method for performing closed loop dialysis treatment comprising: determining an initial ultrafiltration rate and setting an ultrafiltration pump to the determined ultrafiltration rate; measuring a total change in blood volume; determining whether a rate of change in blood volume exceeds a threshold; setting the ultrafiltration pump to a minimum pump rate when the rate of change in blood volume exceeds the threshold; setting the ultrafiltration pump to the determined ultrafiltration rate when the rate of change in blood volume is below the threshold; and stopping the closed-loop dialysis treatment when a cumulative change in blood volume is above a target threshold.

In an exemplary embodiment, the disclosure provides a method for performing closed loop dialysis treatment comprising: (a) determining an ultrafiltration rate; (b) setting an ultrafiltration pump to the determined ultrafiltration rate for an active duration; (c) measuring a total change in blood volume; (d) setting the ultrafiltration pump to a minimum pump rate for a rebound duration; and (e) measuring a rebound change in blood volume. The method further comprises: repeating steps (b)-(e) a first number of times to obtain a regression set, the regression set comprising a number of pairwise values wherein each pairwise value is a measurement of the total change in blood volume and a measurement of the rebound change in blood volume; (f) updating the ultrafiltration rate using the regression set; (g) updating the regression set by repeating steps (b)-(e); and repeating steps (f) and (g) a second number of times, wherein a total duration of one plus the first number of times and one plus the second number of times is a treatment period.

In an exemplary embodiment, the disclosure provides a method for performing closed loop dialysis treatment comprising: (a) determining an ultrafiltration rate; (b) setting an ultrafiltration pump to the determined ultrafiltration rate for an active duration; (c) measuring a total change in blood volume during the active duration to determine when a blood volume waypoint is met; (d) setting the ultrafiltration pump to a minimum pump rate for a rebound duration; (e) measuring a rebound change in blood volume for the rebound duration; and (f) updating the blood volume waypoint. The method further comprises: repeating steps (b)-(f) a first number of times to obtain a regression set, the regression set comprising a number of pairwise values wherein each pairwise value is a measurement of the total change in blood volume and a measurement of the rebound change in blood volume; (g) determining a dry weight time to meet a dry weight goal using the regression set; and (h) determining whether the treatment period is adequate to reaching the dry weight goal.

DETAILED DESCRIPTION

A challenge in providing optimal dialysis treatment is the changes that occur in fluid dynamics as water and toxins are removed from the patient. As fluid levels in the body change, the patient's interstitial space and blood vessels also undergo change. Because there has been no effective, real-time way to measure or model these changes, the standard practice has been to assume a fixed model for the patient based on height, weight, and other physiological parameters established by the practitioner.

In dialysis, one goal is to bring the patient's fluid levels to what is often termed "dry-weight"—generally referring to the amount of fluid that would be in the body if the patient's kidneys were fully functional. A challenge is how to quantify "dry-weight" on any given day, as even people with full kidney function will vary significantly in fluid levels based on diet, activity, hormones, and fluid intake.

In an embodiment, the disclosure provides a method of monitoring actual changes in blood volume during dialysis. The method includes determining how close to dry-weight a patient is by reducing the UF pump rate (the engine which drives dialysis fluid removal) to its minimum setting and monitoring during this "rebound period" to determine blood volume increases (as evidenced by an upward slope) based solely on body re-fill. If there is re-fill, then excess interstitial fluid is present. If the blood volume trace remains relatively flat (slope of zero) during this period, then the patient is near dry-weight for that day.

For purposes of this disclosure, the term "dry-weight" indicates a state in which the blood volume in the vascular space remains virtually constant (near zero slope) when the fluid removal engine of a dialysis system is set to its minimum level. In other words, there is no significant re-filling of the vascular system by stored fluid from the interstitial tissue.

Embodiments of the disclosure provide approaches to adjusting dialysis parameters in real time based on measurements of previously unknown, real-time fluid dynamics of the patient using a blood volume monitor such as the Fresenius Medical Care Crit-Line® monitor as a sensor.

Figure 1:
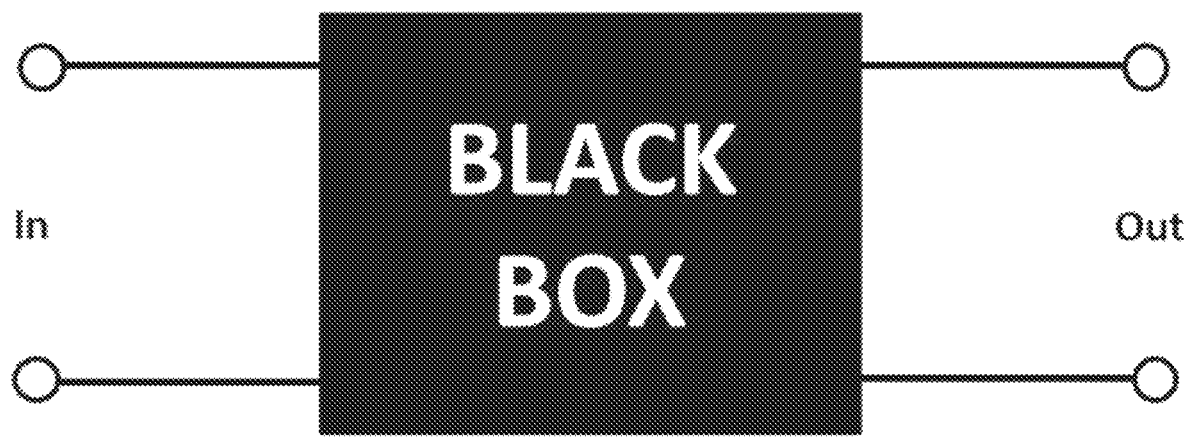
FIG. 1 illustrates an engineering concept of a black box.

Engineering analysis of an unknown system can be accomplished in a number of ways. One variation of a black box method with four terminals is depicted in FIG. 1. Two terminals (left) constitute the input signal into the black box and two terminals (right) constitute the output signal from the black box. In the traditional electrical sense, the black box often simulates an unknown electrical circuit where the internal componentry is inaccessible and undefined. By driving the input of the black box with a regime of known signals controlled in amplitudes, times, and frequencies, while measuring corresponding outputs at the output side of the black box, a function can be derived which characterizes the behavior of the internal circuitry of the black box without ever knowing what specific electrical elements are contained within the black box. Equation 1 describes the transfer function H(A, t, f) or characteristics of how the black box behaves for a given input. Out(A, t, f) is the output sensed at the output side of the black box for a given input driving function In(A, t, f). A, t, and f indicate amplitude, time (also implies phase), and frequency, respectively.

$$H(A, t, f) = \frac{\text{Out}(A, t, f)}{\text{In}(A, t, f)} \qquad (1)$$

According to embodiments of the disclosure, the black box approach is used to monitor the response of the stimulation of the vascular space by the dialysis process. According to embodiments of the disclosure, the black box approach is used to determine real-time fluid dynamics of a dialysis patient under treatment. In an embodiment, dialysis is adjusted based on the response to the stimulation of the patient's vascular space. In another embodiment, the patient's dynamics are modeled to target the patient's dry-weight for the dialysis treatment that day.

By analogy to the electrical circuit described with respect to FIG. 1, a modified black box analysis can be performed to evaluate a patient's physiological fluid response. By measuring the real-time patient fluid dynamics (output), it is possible to tailor the treatment (input) to achieve a particular target fluid removal goal set by a skilled physician or to approach that day's dry-weight.

Figure 2:
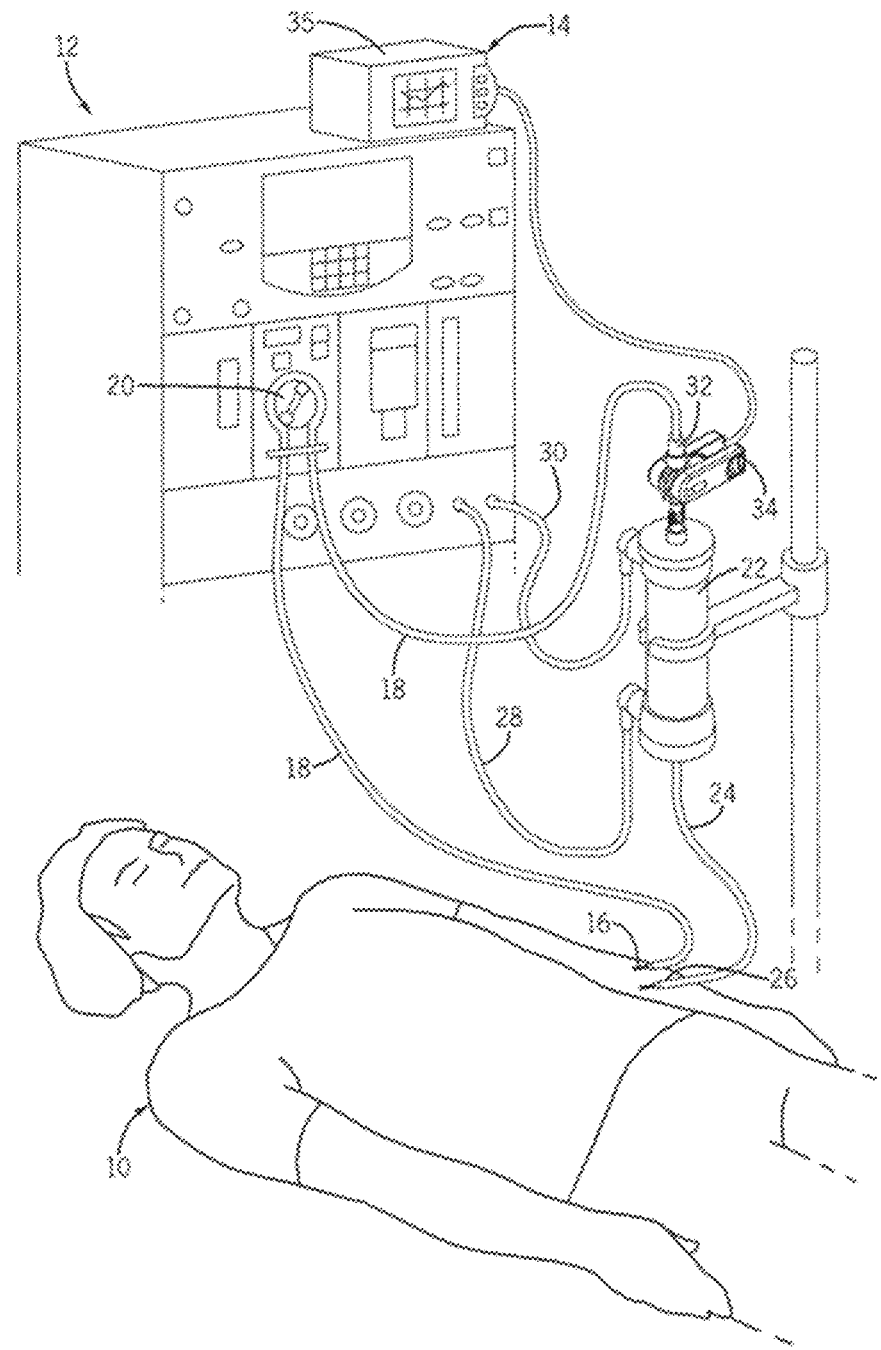
FIG. 2 illustrates a patient undergoing hemodialysis in a clinical setting according to an embodiment of the disclosure.

FIG. 2 illustrates a patient undergoing hemodialysis in a clinical setting according to an embodiment of the disclosure. Dialysis machine 12 renders treatment to patient 10. Hematocrit (HCT) and calculated change in blood volume (ΔBV) percentage as a result of the dialysis process is measured and displayed on blood volume (BV) monitor 14. It is understood that the function of BV measurement can be integrated into the sub-system(s) of dialysis machine 12 but is shown as a separate unit in the example disclosure for clarity.

During dialysis, blood is removed from patient 10 via needle 16 inserted in the patient's surgically implanted access. The blood is routed through tubing 18 driven by peristaltic pump 20 set to a specified blood flow rate under the physician's direction. The blood continues through tubing 18 to blood chamber 32 (used in the measurement of HCT and ΔBV), passes into dialyzer 22, and then back into the patient's body through tubing 24 and needle 26. Fluid removal (and blood cleansing) occurs in dialyzer 22. The dialyzer contains a multitude of internal fibers with pores that allow smaller molecules and water to pass through the fiber walls—but the pores are too small to allow the larger red blood cells and larger proteins to pass. Dialysate solution is separately pumped through tubing 28 into dialyzer 22 and surrounding the fibers within the dialyzer 22. Fluid passes from the blood as waste into the dialysate solution, which exits the dialyzer by tubing 30 to be discarded. This process comprises the ultrafiltration (UF) function of the dialysis system. A separate UF pump is used to pump dialysate fluid into the circuit. The UF rate, along with concentration gradients established by the relative chemical content of the dialysate solution (compared to the blood inside the fibers) promotes movement of excess fluid out of the blood across the membranes. The UF pump rate and the make-up of the dialysate solution are under the direction of the physician.

Embodiments of the disclosure provide a method of monitoring changes in BV using BV monitor 14. In an embodiment, optical sensor 34 of monitor 14 is attached to blood chamber 32 where specific wavelengths of light are shined through the blood as it passes through a viewing window of blood chamber 32. From the absorption and scattering of these wavelengths by the blood constituents, hematocrit (HCT) and oxygen saturation (SAT) are measured by computational system 35 portion of monitor 14. Example models of monitors capable of real-time measurements of blood volume are the Crit-Line® and Crit-Line in Clip (CLiC®) integrated devices.

ΔBV measurements in some embodiments provide advantages over some conventional measurement systems. Conventional systems are based only on a starting signal level passing through the blood at a single wavelength at the beginning of the treatment. Then, successive signal strengths during the treatment are measured to create ratios and are converted into percentages for display. For the purposes of creating a feedback loop to control UF, conventional systems utilizing this approach are inadequate, because the measurements provided are not associated with any actual blood constituents or calibrated parameters. Furthermore, single wavelength optical systems have been shown to be susceptible to false signals from the dialysis system itself. One example of such a false signal may occur where a dialysis system conducts "conductivity tests" by repeatedly measuring dialysate sodium levels throughout a treatment, with large negative spikes in the single wavelength systems appearing as artifacts. If such a system were to be used to control UF, misadjusted UF could occur during a conductivity test of the dialysate, presenting a risk to the patient.

In exemplary embodiments herein, Crit-Line® and CLiC® systems use dual optical wavelengths to measure a calibrated HCT. A dual-wavelength system does not incorrectly react to "conductivity tests" and the resulting HCT is a calibrated indicator of the condition of the blood. Furthermore, using the mass balance provided through the dialyzer filter (no red cells are lost), the HCT (ratio of red cell volume to the total blood volume) is an ideal parameter to mathematically tie the ΔBV indicator to UF. Any control system for deriving ΔBV should be mathematically traceable to one or more calibrated blood parameters if it is to be used for UF control.

By measuring the patient's initial $HCT_0$ and then comparing successive $HCT_m$ readings during dialysis, it is possible to calculate the actual change in blood volume assuming no red blood cells are lost in the dialysis process and the red blood cell volume remains in mass balance. From the definition of HCT, the percentage change in blood volume based on HCT is given by Equation 2.

$$\Delta BV(\%) = \left[\frac{HCT_0}{HCT_m} - 1\right] \times 100\% \qquad (2)$$

where ΔBV (%) is the HCT based relative change in blood volume from the beginning of the treatment, $HCT_0$ is the beginning HCT of the treatment, and $HCT_m$ is the real time measured HCT during the treatment.

Figure 3:
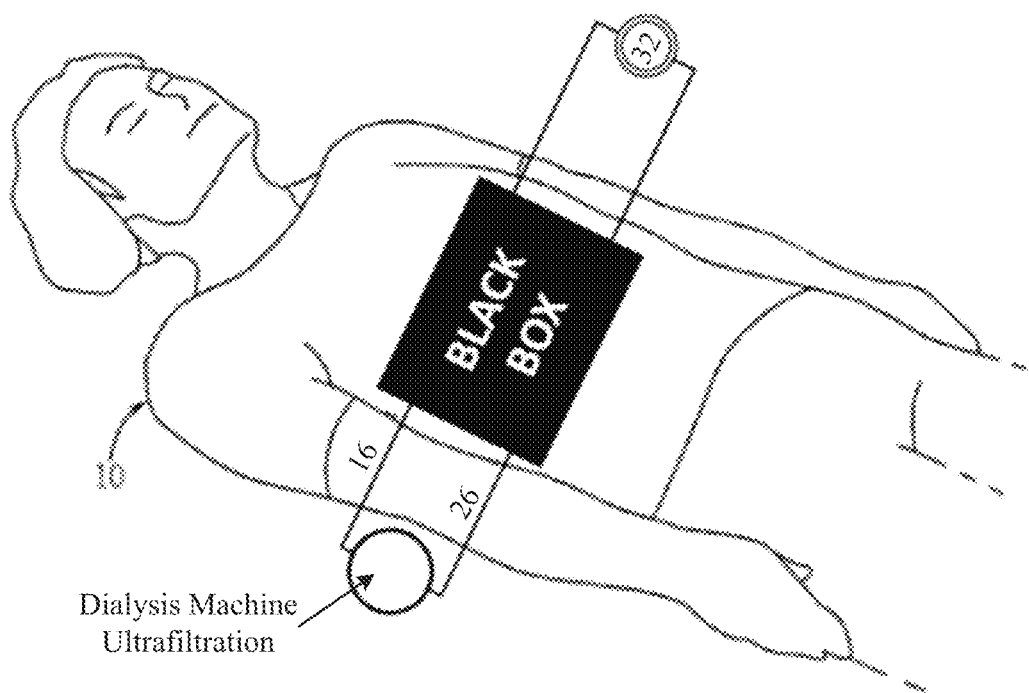
FIG. 3 illustrates the concept of the black box being applied to a patient undergoing hemodialysis according to an embodiment of the disclosure.

With the dialysis system rendering treatment to the patient (controlled signal Input) and the Crit-Line® system monitoring the resulting blood volume change (Output signal), the black box method can be applied to the patient as shown in FIG. 3. The black box represents the internal fluid dynamics system of the patient—which otherwise cannot be easily characterized by outside means. Using an analogous approach to the electrical black box analysis described earlier, the patient's fluid dynamic conditions can be measured and, therefore, characterized by driving the system through the dialysis treatment based on UF adjustment, and at the same time, monitoring the effects of that drive in the resulting blood volume change.

By using a blood parameter based measurement to characterize the dialysis treatment output from the patient's black box fluid model (e.g. ΔBV based on calibrated HCT), this real time measurement can be used to control the input parameter(s) of the dialysis system (e.g. UF, treatment time, sodium in the dialysate, etc.) in a closed loop, avoiding some of the limitations created by the uncertainty in exact fluid dynamics that can occur internally in a patient presenting for treatment or in the patient during the course of treatment. The following examples further illustrate embodiments of the disclosure, but should not be construed as limiting the scope of the disclosure.

Example 1

Single Target Linear Blood Volume Reduction

In an exemplary embodiment, a method is disclosed where the patient's fluid removal profile can be estimated based on sufficient historical data. From the types of medical factors affecting the patient, the physician uses calculations, algorithms and/or experience-based judgement to determine a fluid removal target for the patient's dialysis treatment. In the embodiment, the physician seeks to provide a treatment that achieves and maintains, on an ongoing basis, the patient's estimated dry-weight. The physician prescribes a target ΔBV for fluid removal and specifies it to the clinical staff managing the patient's care. For instance, the physician may estimate the required blood volume removal to be 15% over a three hour treatment. In this scenario, an initial estimated UF rate is programmed into the closed-loop dialysis system by a clinician—also as directed by the physician order.

Figure 4:
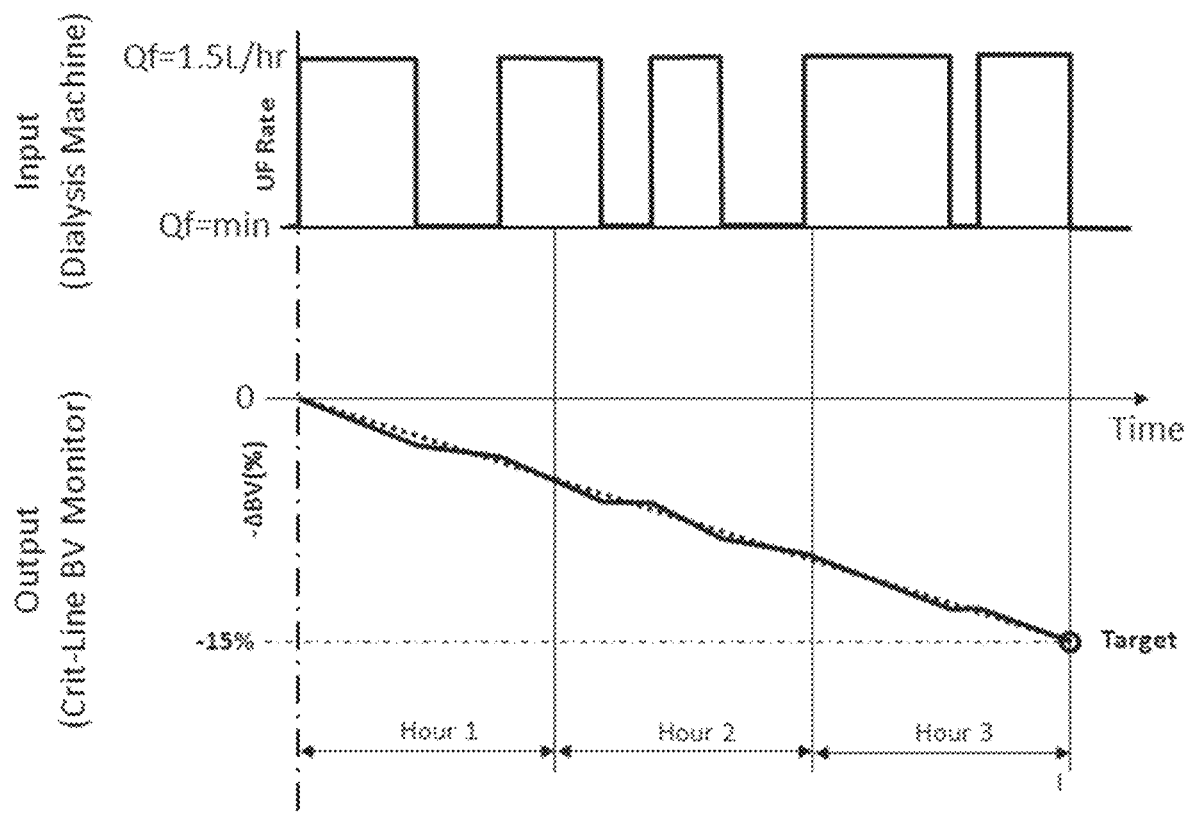
FIG. 4 illustrates dialysis machine flow rate input and output (as measured, for example, using Crit-Line® sensors) of a blood volume monitor according to an embodiment of the disclosure.
Figure 13:
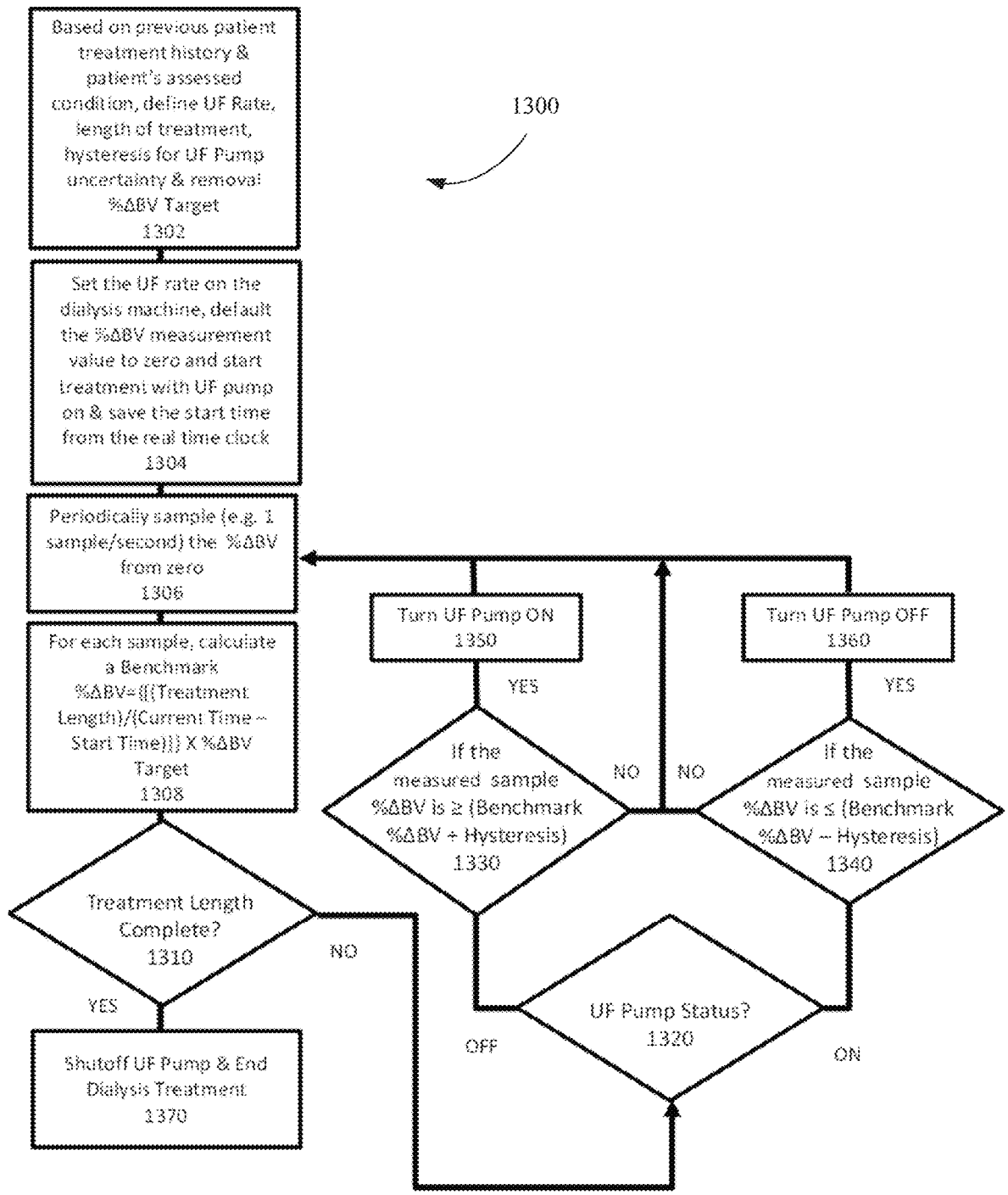
FIG. 13 is a process flowchart of a dialysis treatment according to an embodiment of the disclosure.

In the Example, blood volume monitor 14 (as shown in FIG. 2) is programmed to remove a linear 5% per hour of blood volume. Blood volume monitor 14 controls the UF pump rate to ensure that fluid removal follows the linear trajectory until 15% blood volume is removed at the end of the three-hour treatment per physician's order. FIG. 4 illustrates the resulting blood volume trace as it might appear on the hematocrit-based blood volume monitor 14. This trace is used in real time for UF pump cycle duty control. In this example, by varying the UF pump duty cycle programmed in dialysis machine 12, the UF pump operational and pause times drive fluid removal to the specified target trace. (This process is illustrated in the flowchart of FIG. 13, with detailed description later enclosed).

Using a different method, the trajectory of the ΔBV trace can be adjusted through the actual UF pump rate, also under computer control, driving dialysate system 28, 30 for dialyzer 22. This is an alternative method to cycling the UF pump on and off, with the UF level held at a fixed rate (as shown in FIG. 4). Both approaches rely on feedback from blood volume monitor 14 and a controller to couple and condition the monitoring system feedback signals to the pump controller. In a different application, cycle times and UF rate can both be adjusted together to control the UF rate and timing to match the desired trajectory of fluid removal. For example, after a pause of the UF pump during the re-filling cycle of monitoring reveals that the patient's body is re-filling at a faster than expected rate, the UF pump may then be configured to run at a higher rate, increasing osmotic pressure on the dialyzer and pulling more fluid out of the patient's bloodstream. This change in the UF rate may be made automatically by the system or may be confirmed by the clinician as a desired course of action based on the data presented.

In another embodiment, UF parameters as well as sodium level in the dialysate used for reverse osmosis across the dialyzer can be adjusted to affect the fluid removal rate to meet the specified target. To use the sodium modeling, the tolerance of the patient to variations in sodium is used to establish safety boundary conditions. Unlike the direct feedback to control the UF pump examples using only blood volume as a feedback, the sodium modification approach utilizes known sodium reaction mechanism modeling of the patient to be well defined by the physician through repeated patient treatment analysis prior to automated sodium feedback implementation, or some form of direct blood sodium measurement is used to augment the blood volume based feedback.

In this Example 1—Single Target Linear embodiment using a linear trajectory feedback of UF pump control, the linear trajectory is assumed to be the best course for the patient, and there is no effort to account for differences in the physiology of the patient or fluid dynamics of the patient's body at various times during treatment.

When using a feedback system where a trajectory to a designated end blood volume is programmed, real time measurements by blood volume monitor 14 are compared to the time-based target along the trajectory at regular intervals (for example, every second). As the measured blood volume becomes very close to the desired trajectory points, oscillations will occur in dialysis machine 12 blood pump, causing undue wear and tear on the pump and controller circuitry. The dynamic blood volume parameter is constantly changing and when that parameter approaches or reaches the current target level it will not remain at that level without further adjustment.

In the plot of the UF pump activity shown in example FIG. 4, a hysteresis band is implied in the graphs. The dotted line is the plot of the ideal target trajectory points and the solid line shows anticipated actual blood volume trajectory based on the programmed allowable hysteresis around the ideal target points. It is noted that the cycle on time of the UF pump is shown to overshoot slightly to the negative of the target dotted lines and that during the cycle off time, the trace is shown to allow re-filling to a slightly positive side of the dotted target lines. A system designed to operate in closed-loop fashion such as presented in this Example may have the ability to program acceptable hysteresis bands around the absolute target values to prevent unacceptable UF pump oscillations "on and off" at the sample points.

Example 2

Multiple Target Blood Volume Based on Trajectory Estimates

In an exemplary embodiment, a method is disclosed where the patient's fluid and treatment profiles can be estimated based on sufficient historical data. As in Example 1, medical factors previously described are used by the physician in calculations, algorithms and/or experience-based judgement to determine how excess fluid should be removed.

Example 1 assumed that the specified change in blood volume followed a linear function of simple fluid removal with a single ΔBV trajectory to achieve that target. In Example 1, the body is assumed to be able to withstand a blood volume reduction at a constant rate, and fluid removal accordingly follows a single volume removal line.

In practice, the patients' fluid interchangeability alters as fluid is removed. At a minimum, tissue spaces undergo changes, and the ability of the vascular system to transfer fluid changes in response to fluid dynamics. The physician strives to achieve and maintain on an ongoing basis the patient's estimated dry-weight. The physician may prescribe multiple targets during a treatment for affecting fluid removal to best estimate how the dialysis treatment should be completed based on professional judgement and/or data from previous experience with the patients' fluid change capability. The physician then specifies these milestone targets through the duration of the treatment to the clinical staff. In an example, the physician may estimate that the overall required blood volume to be removed is 12% over a three hour treatment. Unlike the linear feedback approach of FIG. 4, however, based on experience with this patient's ability to tolerate UF and other parameters measured in the lab, office visits and through metrics taken the day of the treatment, the physician estimates what removal rate the patient can tolerate. The physician then prescribes a dialysis regime (i.e., profile) for minimum impact to the patient.

In this example, the physician estimates and specifies that the patient's body can tolerate a 7% removal blood volume reduction over the first hour, running at a UF rate of 1.2 L/hour. In the second hour, an additional 3% reduction is targeted. During the last hour, an additional 2% is removed.

Figure 5:
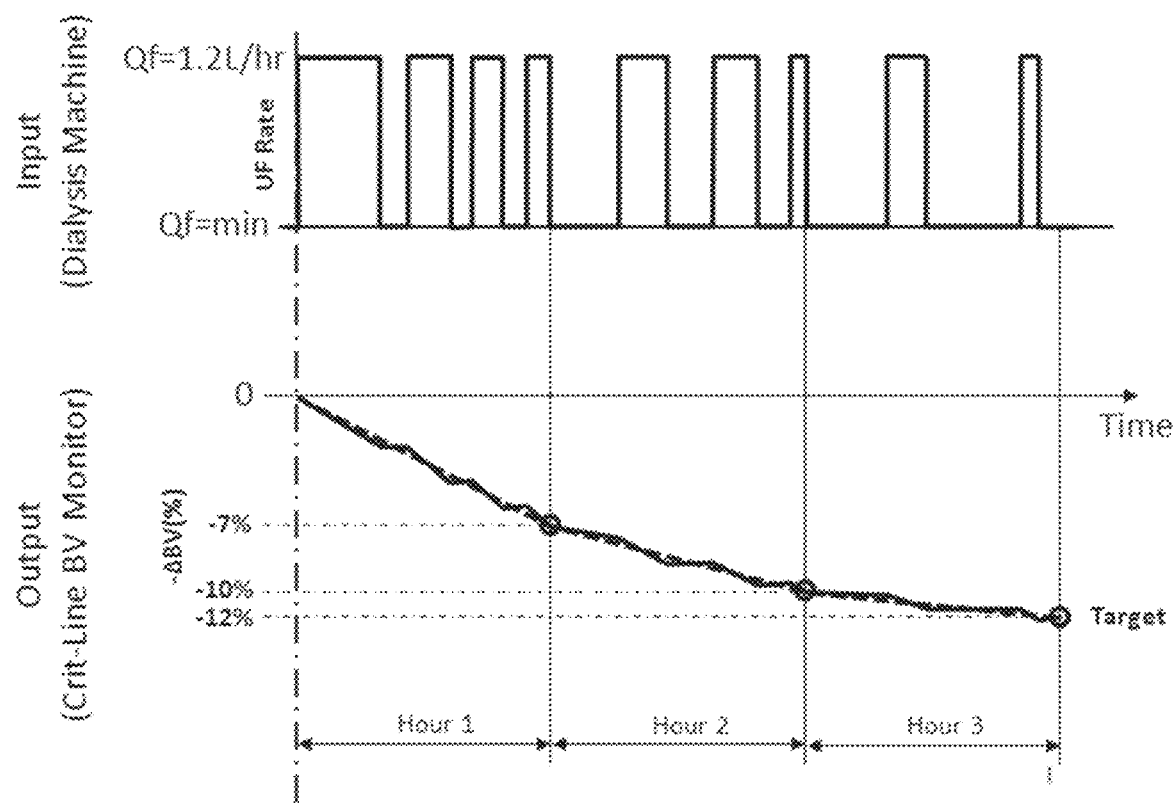
FIG. 5 illustrates dialysis machine flow rate input and output of a blood volume monitor according to an embodiment of the disclosure.

Blood volume monitor 14 (see FIG. 2) is programmed to follow the outlined trajectory profile and will control the UF cycle time to ensure fluid removal follows this trajectory until the entire 12% blood volume is removed by the end of three hours. In another embodiment, the monitoring system can change the UF rate—either independently or in conjunction with the cycle time of the UF operation of dialysis machine 12. FIG. 5 illustrates the described sample case where UF rate is cycled on and off to follow the prescribed trajectory (refer to the flowchart in FIG. 14 and detailed description thereof later enclosed). FIG. 5 illustrates the resulting blood volume traces based on UF cycle control, using dialysis machine 12 and hematocrit based blood volume monitor 14 to control the UF cycle time to drive fluid removal to the specified target. The trajectory can be controlled by adjusting the UF rate driving dialysate system 28, 30 for dialyzer 22 of dialysis machine 12. Alternatively, the UF can be cycled on and off at a fixed rate. It is also possible to combine with an appropriate algorithm the UF rate and pump cycle times to meet the trajectory. All approaches rely on controller and software feedback from blood volume monitor 14.

As with Example 2, another embodiment may vary sodium level in the dialysate if appropriate and safely modeled. This approach could be used either alone or in conjunction with the variation of UF rate (and/or UF time). To use the sodium modeling, the tolerance of the patient to variations in sodium is utilized to establish safety boundary conditions. Unlike the direct feedback to control the UF pump examples using only blood volume as feedback, the sodium modification approach utilizes known sodium reaction mechanism modeling of the patient to be well defined by the physician through repeated patient treatment analysis prior to automated sodium feedback implementation, or some form of direct blood sodium measurement is used to augment the blood volume based feedback.

In this Example 2 embodiment, the treatment waypoints in the programmed trajectory are designated by the physician to be representative of the best course of fluid removal for the patient for the current treatment. It may not be entirely possible to characterize a patient's condition on any given day, due to changes in lifestyle or other physiological factors that are not easily modeled. For example, the described treatment regime illustrated in FIG. 5 may be used on a patient during a Friday session, with the treatment regime matching the patient's body requirements very well. The patient then may go home feeling better than usual. Over the weekend, the patient might overindulge in food and/or drink as a result. When the patient returns to the clinic on Monday, the treatment profile trajectory may need to be radically different than what worked well on Friday. However, using different targets at different intervals along the overall treatment trajectory is estimated to be better than a simple linear approach as described in Example 1, if the targets of what the patient can tolerate are accurate.

There is evidence to support the multiple target approach of Example 2 through analysis of morbidity events and deaths in the patient population. These data suggest that certain percentage ranges of fluid removal at specific times in the treatment are more effective in preserving patient health than other estimation methods. Accordingly, specific ΔBV target zones may be targeted for the end of each hour.

Figure 6:
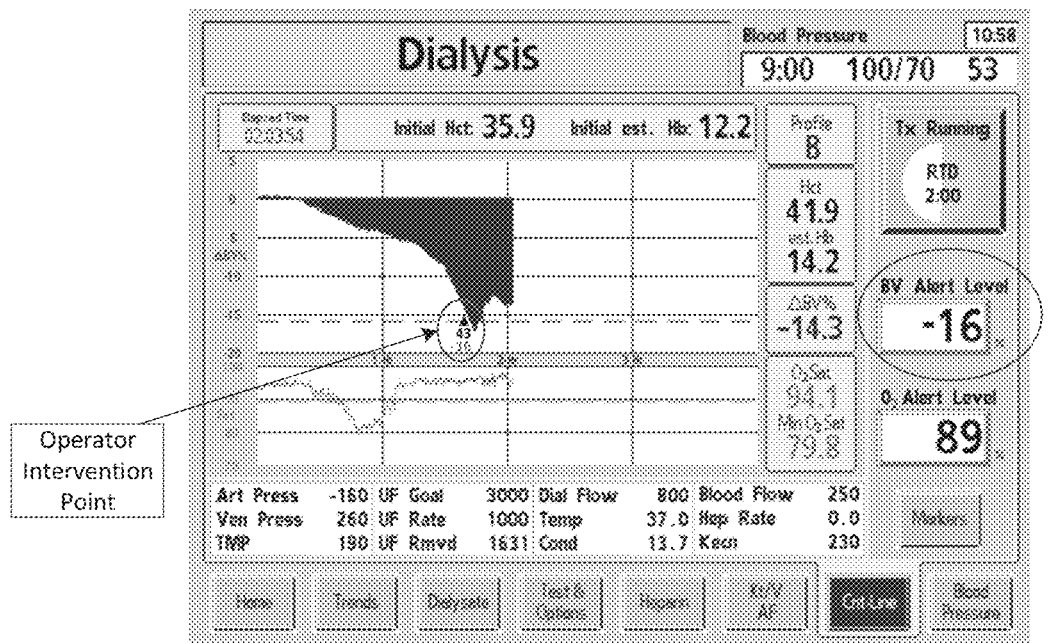
FIG. 6 illustrates a screenshot of a monitor showing change in blood volume during dialysis according to an embodiment of the disclosure.

Adaptively following a ΔBV trajectory presents several advantages over conventional methods. Conventional methods require a clinician to monitor the dialysis system during hemodialysis. For example, a dialysis system may have a screen display showing patient fluid removal progress in terms of the patient's ΔBV (or HCT) profile as shown in FIG. 6. As shown, the screen display shows that the operator is allowed to set a BV alert level so if ΔBV falls below the BV alert level, an alarm is sounded for intervention. If the alert level is reached, the feedback from blood volume monitor 14 can disable the UF pump in dialysis machine 12 to prevent too much fluid being removed during the overall treatment and causing potential morbidity event.

The screen displays a profile that indicates the percentage change in the ΔBV. At least three conditions can be gleaned from the screen: whether a patient is re-filling too fast such that too little fluid is being removed to meet UF target goal, whether UF rate is in an acceptable range where fluid is being removed at a rate capable of meeting target UF goal, and whether UF rate is too high such that the change in blood volume will overshoot the removal goal(s) and the patient may begin experiencing morbidity events such as cramping or nausea.

Figure 7:
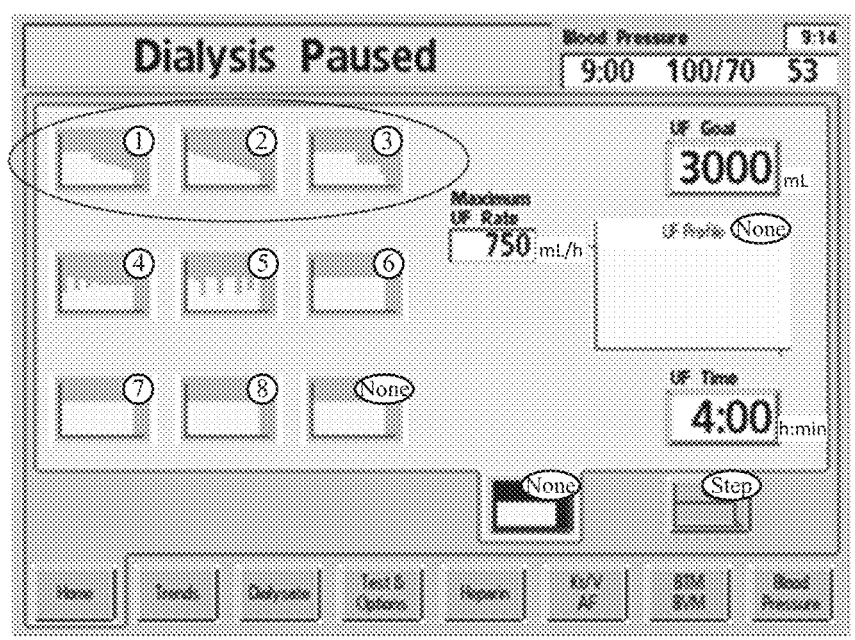
FIG. 7 illustrates a screenshot of a monitor showing choices of pre-defined UF profiles according to an embodiment of the disclosure.

If under the multiple target embodiment of Example 2 the UF profiles are found to be repeatable for a broad patient base, dialysis machine 12 can be configured with pre-defined UF profiles to be selected by the clinician during the patient treatment setup as shown in FIG. 7. The UF pump rates and timing between profile changes provide the baseline UF pump activity of dialysis machine 12 while blood volume monitor 14 modifies and adapts this base profile to meet the trajectory targets during the treatment. The initial maximum UF rate is calculated based on the UF Goal and UF Time. The preset profiles in dialysis machine 12 with modification in real time of the baseline presets by blood volume monitor 14 is one embodiment of Example 2 which could also be applied to Example 1.

An alternate embodiment simply utilizes an initial UF rate being set in dialysis machine 12 and blood volume monitor 14 controls the overall profile and adaptation of the UF rate to the targets along the programmed trajectory completely under software control.

In conventional methods, dialysis systems can sound an alarm when the change in BV exceeds a predefined BV alert level, but the handling of the alarm requires manual intervention by the operator to adjust the ΔBV rate by changing the UF pump rate or administering a saline bolus to increase blood volume. However, administering a saline bolus is non-optimal because it adds additional fluid volume that will need to be removed later.

If available on dialysis machine 12, the UF pump profiles 1, 2, and 3 in FIG. 7, which decrease the UF rate over time, appear to be most suitable for use as a baseline trajectory target attainment while preventing large drops in blood volume toward the end of treatment.

Not all dialysis machines contain predefined UF pump profiles. The preferred embodiment is to control the attainment of program trajectory targets through software control by BV monitor 14 of the UF pump characteristics in real time. One advantage of this feedback system is elimination of manual clinician interventions during the treatment.

Example 3

Blood Volume Control Based on Real-Time Patient Fluid Dynamics

Examples 1 and 2 administer closed loop dialysis to specific targets of blood volume removal, where the targets are best estimations of what the patient requires to approach dry-weight. These estimations are based on patient history, lab measurements, weight at the time of presenting for the dialysis treatment and the like. Due to the dynamics of patient fluid conditions, the estimations may or may not represent the patient needs for a particular day's treatment due to something as simple as a departure from normal food and drink intake in the days prior.

In an exemplary embodiment, a method is disclosed that stimulates controlled, real time changes in input (dialysis UF pump parameters) to the patient's body which results in the response of the patient's vascular system as output monitored in the change in blood volume measurements as fluid is removed. Measurement of these differentials allows the clinician to establish the patient's fluid dynamics specifically, and to perform further assessments during treatment. The general equation for this differential black box analysis of the patient's dynamic system is given in Equation 3.

$$H'(UFR, t) = \frac{\Delta Out(UFR, t)}{\Delta In(UFR, t)} \quad (3)$$

H'(UFR, t) is the transfer function (characteristics) of how the black box output behaves for a given input. Out(UFR, t) is the output sensed at the output pins for a given paired input, and In(UFR, t) is the input driving function with an amplitude, time (also implies phase) and frequency. The In(UFR, t) function may be generated by setting up a specific and repeating profile of drive to the patient's system using the UF pump controller of the dialysis machine, which results in a stimulated blood volume response, Out(UFR, t), measured by the blood volume monitor. This could be controlled by either a pre-set of dialysis machine 12 profile, if available, or governed by software control of blood volume monitor 14. Sufficient samples produced by this approach allow for ongoing, real-time measurement of the body's fluid dynamics during dialysis—including resultant changes caused by fluid removal itself.

In an example, a physician may prescribe a specified UF rate, $Q_f$, based on the total fluid volume to be removed from the patient. The treatment is to take place over a period of 3 hours. The establishment of the initial $Q_f$ rate is based on the same criteria as described in Examples 1 and 2, including past patient treatment tolerance, lab measurements, physical examinations, weight at time of presenting for dialysis, and the like. In an embodiment, dialysis treatment involves bringing the patient as close to his or her dry-weight for that particular day as possible, while recognizing that every time the patient undergoes treatment, he or she can vary in starting conditions based on activities and food/drink intake since a previous treatment.

Figure 8:
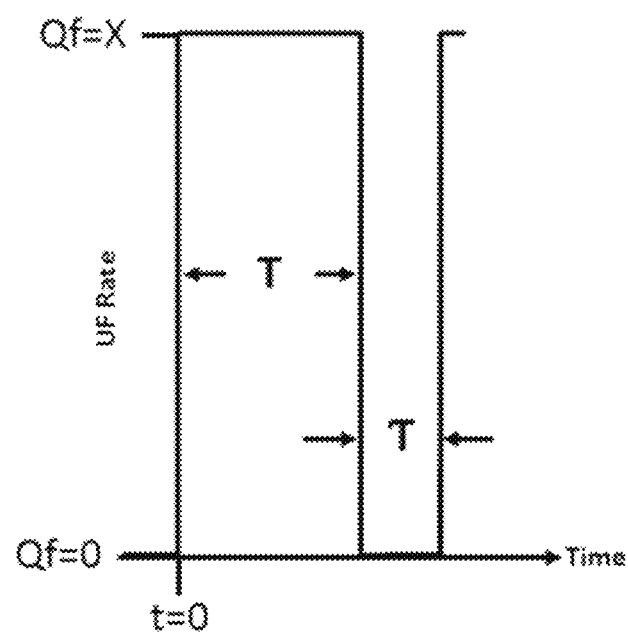
FIG. 8 illustrates a single cycle of UF driving according to an embodiment of the disclosure.

In an embodiment, the patient's body is stimulated by dialyzing at a fixed rate for a designated period of time (T) at UF pump rate $Q_f$. The blood volume change is monitored and recorded. At the end of the period T, the UF pump rate $Q_f$ is set to zero or the minimum level possible (based on dialysis machine design). Then the change in blood volume without a UF driving function (refill reaction of the patient's physiology) is measured and recorded during a fixed time period (T). FIG. 8 illustrates a single cycle of UF driving according an embodiment. In FIG. 8, the UF rate is cycled between a minimum UF pump rate $Q_f=0$ and a UF rate $Q_f=X$. In an ideal response, the re-fill of the vascular system from the internal tissue during the UF off trace (T) on the blood volume monitor will remain constant (flat) with no upward trend (no re-filling taking place—at or near dry-weight). This ideal response during the UF off trace can be used as a stopping condition.

Example 3 differs from other feedback-based dialysis techniques. For example, the fluid dynamics of the body were either able to withstand blood volume reduction at a constant rate in Example 1 or the fluid dynamics and patient tolerance were estimated in Example 2 for each treatment. In Example 3, applying treatment in cycles as shown in FIG. 8, the dialysis machine provides the UF driving function by removing blood volume at a specific rate $Q_f$ during time T. The black box in FIG. 3 represents the unknown characteristics of the patient's fluid dynamics. In FIG. 3, the input side of the black box indicates stimulation from a dialysis machine ultrafiltration while the output side of the black box indicates output signals measured at blood chamber 32 by blood volume monitor 14. A UF pump driving function with a profile corresponding to FIG. 8 is programmable in some dialysis machines. The output signal of the black box is monitored by a change in blood volume during time T as measured by, e.g., a Crit-Line® or other hematocrit based blood volume monitor. Then the cycle is repeated throughout the dialysis treatment.

In an example (and it is recognized that T and T can be other values), T=15 minutes and T=5 minutes. The total cycle time for the waveform of FIG. 8 is 20 minutes and, therefore, three of these cycles occur per hour of treatment. The value of T is chosen to be long enough for the UF to stimulate the body with a non-zero change reduction in ΔBV The time T should be long enough to observe the re-fill response due to the UF stimulation during time T.

The fluid removal instruction by the physician, in this example, is to remove fluid at rate $Q_O$ for the three hour treatment (based on similar criteria outlined in Examples 1 and 2). This value of $Q_O$ may be adjusted for use in various embodiments, as described in Example 3. Since UF will be active only 45 minutes of every hour based on the selection of times T and T, the initial UF rate, $Q_f$, is adjusted per Equation 4 for a 3 hour treatment.

$$Q_f = \frac{Q_0}{\left(\frac{\text{Time with } UF \text{ On}}{\text{Original Treatment Time}}\right)} = \frac{Q_0}{\frac{135 \text{ minutes}}{180 \text{ minutes}}} = 1.33 Q_0 \quad (4)$$

For example, if the originally-prescribed UF rate, $Q_0$, was specified as 1500 ml/hr, then for the proposed driving function shown in FIG. 8, the adjusted initial ultrafiltration rate, $Q_f$, will be set at 2000 ml/hr. The alternating of the dialysis treatment between 15 minutes of ultrafiltration at 2000 ml/hr to 5 minutes of ultrafiltration at minimum (~0 L/min) over the treatment time is represented by the patient black box fluid physiology model shown in FIG. 3. In FIG. 3, the driving UF waveform of FIG. 8 is applied to the patient's body and the responses are measured by a hematocrit based blood volume monitor.

Figure 9:
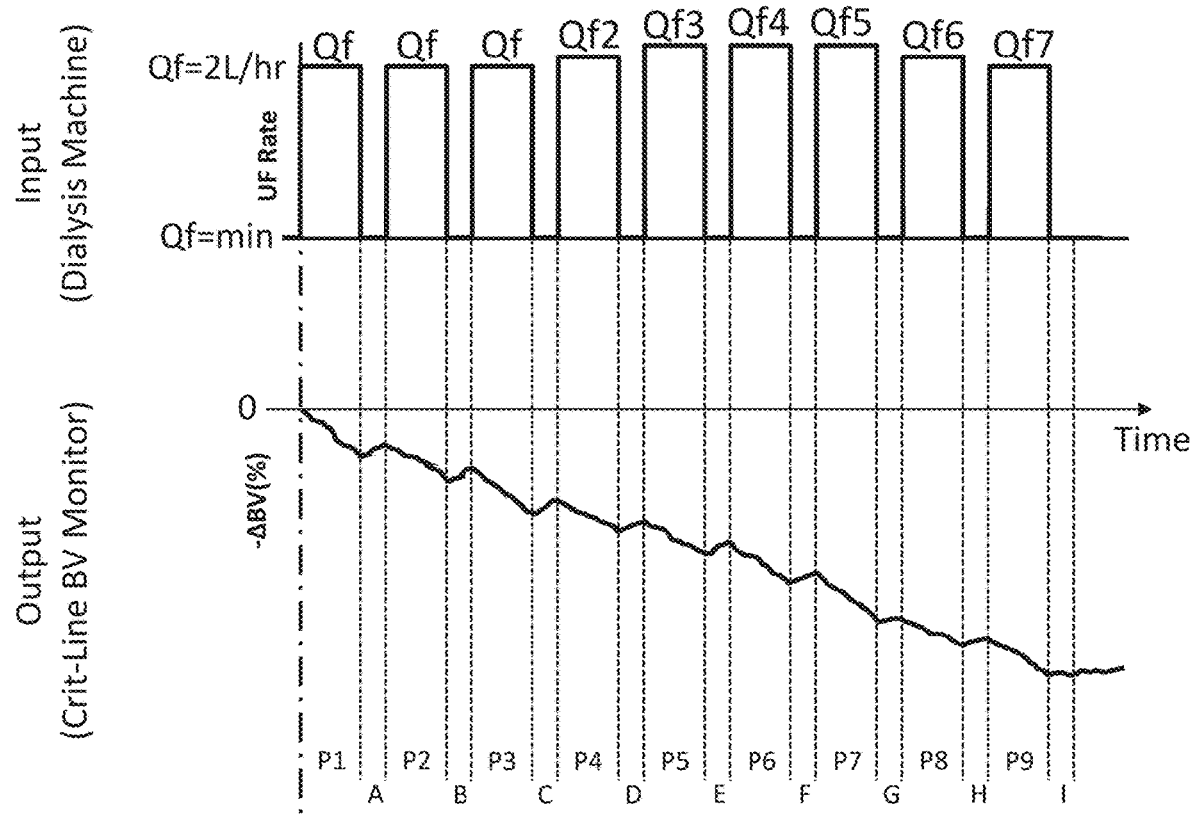
FIG. 9 illustrates a treatment profile for a patient undergoing dialysis according to a time based embodiment of the disclosure.

The output of the patient's black box fluid physiology is manifest in the responses to the UFR step driving function, as reflected in the change in blood volume during the 5 minute response periods at minimum UFR. FIG. 9 illustrates an example of this concept. In FIG. 9, time periods P1-P9 are all 15 minutes in duration. Time periods A-I are all 5 minutes in duration. The total time for P1-P9 and A-I spans the designated 3 hour period of the dialysis treatment. A 3 hour treatment period is used as an example, but the treatment period may be longer, perhaps even up to 8 hours in countries outside the United States. In FIG. 9, the ultrafiltration rate $Q_f$ is initially set at 2 L/hr (see Equation 4) to meet the beginning fluid removal goal specified by the original ultrafiltration rate $Q_0$ of 1.5 L/hr due to the modified duty cycle of the ultrafiltration time period. The initial 2 L/hr is the starting point for treatment according to an embodiment of the disclosure.

Since dialysis treatment aims to remove fluid to the approximate point where the patient will have kidney function, a target for the change in blood volume in the rebound period I is ΔBV (I)=0. The ΔBV (I)=0 flat rebound measurement indicates that there is minimal to no refilling into the vascular space by fluid stored in the internal tissue of the patient. In some embodiments, the patient cannot tolerate a zero rebound rate so an acceptable non-zero rebound slope target is set in period I. In other embodiments, additional follow-on treatments may be utilizes to achieve dry-weight goals over an extended period of days, weeks or even months, depending on the patient's tolerance.

Suppose, for simplicity, that zero rebound is desired during period I. The following discussion provides an embodiment of how the treatment profile of FIG. 9 can be used to integrate the measured fluid dynamics of the patient during treatment. In a time based embodiment, a zero rebound goal is reached through a series of successive regressions to determine the function H'(UFR, t) in Equation 3 for a given set of 3 successive cycles shown in FIG. 9 (beginning with cycles P1, A; P2, B; and P3, C). In this example, H'(UFR, t) is modeled as a second order polynomial which utilizes three ordered pairs of data points. In the example with 15 minute treatment intervals and 5 minute rest intervals, the three ordered pairs of data points occur over the course of one hour. Other time intervals may be used based on the insight of those skilled in the art. However, for this embodiment, once defined the time intervals are held constant.

The abscissa numbers for the initial 3 cycles will be the sum of the blood volume changes measured in each period of active UF. For the first regression, the first X value, X1, will be the change in blood volume in period P1. The second X value, X2, will be the sum of X1 plus the change in blood volume measured in period P2. The third X value, X3, will be the sum of X2 plus the change in blood volume measured in period P3.

The ordinate numbers for the initial 3 cycles will be the individual changes in blood volume measured when the UF is not active. For the first regression, the first Y value, Y1, will be the individual rebound change in blood volume in Period A. The second Y value, Y2, will be the individual rebound change in blood volume in Period B. The third Y value, Y3, will be the individual rebound change in blood volume in Period C.

The first solution, finding $H_1'(UFR, t)$ is found by regressing the ordered pairs (X1, Y1); (X2, Y2); and (X3, Y3) using numerical analysis methods to produce a second order polynomial characterizing how the refill rate of the patient is responding to successive changes in blood volume resulting from the dialysis treatment.

The resulting polynomial will be of the form:

$$Y = aX^2 + bX + c \quad (5)$$

Y is the desired target rebound (zero being an indication of near dry weight). X is the relative percentage of fluid removal as measured on the Crit-Line® or similar device as the % ΔBV which is proportional to Time×UF rate. By setting (5) equal to zero for Y (no rebound~dry weight) X can be solved for. Dividing X by the time remaining in the treatment to time period I, the UF rate required can be solved for and adjusted on the machine. This can be done manually or through software control.

It is noted that an X value (change in patient overall blood volume due to active UF) is the area found between the trace in a given period and the zero axis. This area is a function of UF rate $Q_f$ and elapsed time (e.g. P1, P2, . . . P9). Therefore, the volume dialyzed is a function of the UF rate and the time periods UF is active. In this embodiment, the time periods remain fixed while the UF pump rate is considered variable.

Based on the regressed $H_1'(UFR, t)$ polynomial, the expected fluid rebound at Period I can be determined. The fluid rebound is a measure of how much fluid is left in the body above the normal blood volume level as if the patient had kidney function. The rebound amount is a function of how much fluid has been removed from the body under the dialysis process. Therefore, the regressed function $H_1'(UFR, t)$ relates the rebound caused by vascular re-filling to the amount of fluid removed by the dialysis treatment to the point in time these measurements are made.

If the rebound level is greater or less than zero (the dry-weight target) then the regressed equation is set equal to zero for the rebound value at Period I (dry-weight target) and the cumulative ΔBV amount required to be removed over the total period to Period I is solved for. From this cumulative ΔBV amount and the active UF time remaining during the rest of the treatment through P9, a new modified UF rate $Q_{f2}$ is calculated and then adjusted on the dialysis machine. Since the time periods are designated as being fixed in this embodiment, the $Q_{f2}$ adjustment is based on a proration over the active UF periods remaining in the treatment to the three active UF periods total ΔBV to this time point in the analysis.

After X1-X3 and Y1-Y3 are regressed and analyzed and $Q_{f2}$ is adjusted, the next cycle of dialysis is completed, yielding data for blood volume removed during P4 and the rebound amount in period D. These measurements form another ordered pair (X4, Y4) where X4 is the sum of X3 plus the blood volume change from P4 and Y4 is the rebound value measured with UF inactive in period D.

Ordered pair (X1, Y1) is then dropped from the analysis and ordered pairs (X2, Y2); (X3, Y3); and (X4, Y4) are then regressed to find the second solution $H_2'(UFR, t)$. Based on the regressed $H_2'(UFR, t)$ polynomial, the expected fluid rebound at Period I can again be solved for. If the rebound level is greater or less than zero (the dry-weight target) then the cumulative ΔBV amount is derived to yield a zero value for the T period rebound at period I based on the regression equation. From this cumulative ΔBV amount and the active UF time remaining during the rest of the treatment through P9, a new modified UF rate, $Q_{f3}$, is calculated and the adjusted on the dialysis machine. Since the time periods for this example are designated to remain fixed, the $Q_{f3}$ adjustment is based on a proration over the remaining active UF periods remaining in the treatment to the three active UF periods total removed blood volume to this time point in the analysis.

The cycles of dialysis and regression analysis may continue through all successive periods, i.e., through P9 and I. However, in some embodiments, regressions are only meaningful through the solution to $H_6'(UFR, t)$ since no adjustment can be made after this time period that will affect the outcome in Period I.

By this last period, the rebound during the UF off time in Period I will be close to zero. If the physician elects to allow a rebound amount other than zero by the end of treatment, then the solutions to the successively regressed characteristic equations, $H_1'(UFR, t)$ through $H_6'(UFR, t)$ can target the designated rebound slope during the UF off Period I by yielding alternate $Q_f$ values appropriately. Note that in FIG. 9, P1-P3 have the same $Q_f=2$ L/hr while P4 through P9 each have different values of $Q_f$: $Q_{f2}$ to $Q_{f7}$ based on $H_1'(UFR, t)$ through $H_6'(UFR, t)$.

Example 3 provides embodiments of how dialysis can be adapted with hematocrit based BV monitoring to incorporate the patient's real-time fluid dynamics into the dialysis treatment on a given day. Incorporating real-time fluid dynamics provides for improved outcomes, reduced stress to the patient, and a more efficient way of regulating ultrafiltration rate.

Furthermore, in some embodiments, the regression data derived by patient fluid dynamic feedback can be used to glean other information. The coefficients a, b and c of the equations in the form of shown in Equation 5 of the regressions $H_1'(UFR, t)$ through $H_6'(UFR, t)$ can be tabulated by patient and treatment time slice. Analysis of these coefficients over multiple treatments can be used to characterize the general fluid dynamics over time of treatment for a specific patient. These data can then be used by the physician to better understand the respective patient's physiology with respect to treatment tolerance and profile.

Figure 10:
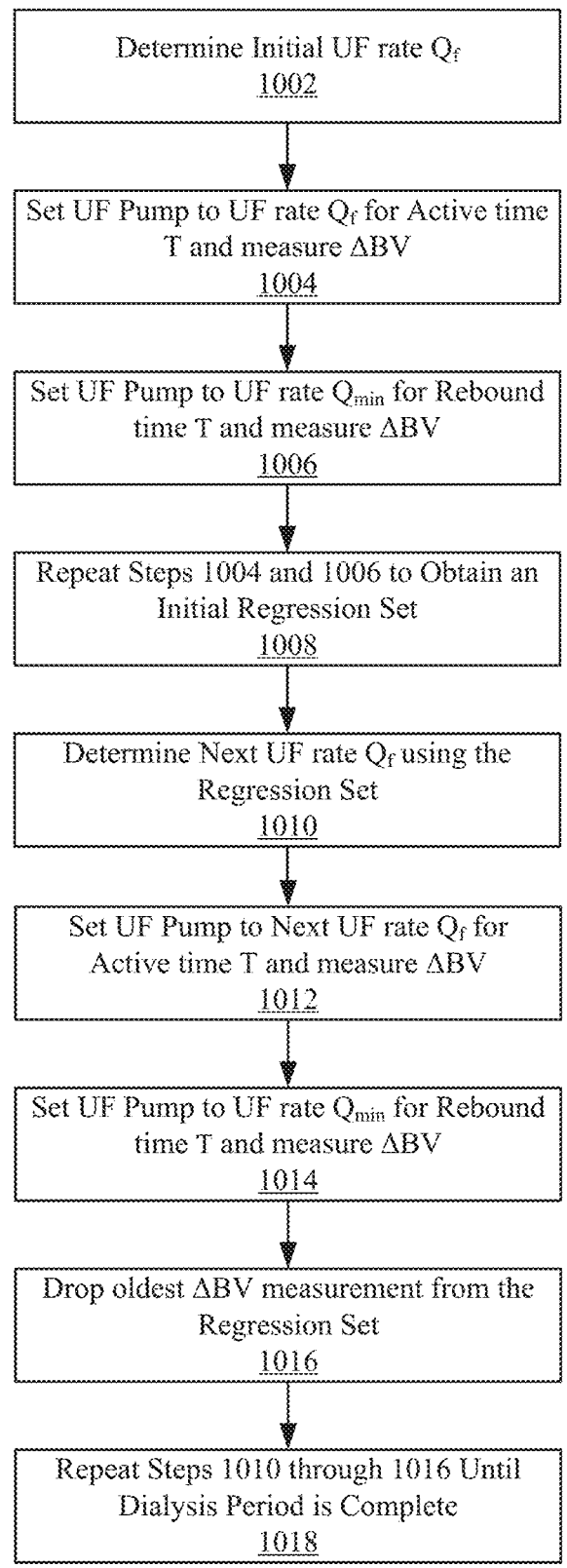
FIG. 10 is a process flowchart of a dialysis treatment using constant time intervals according to an embodiment of the disclosure.

FIG. 10 is a flowchart of a closed-loop dialysis treatment according to an embodiment of the disclosure. At stage 1002, dialysis system 12 determines initial UF rate $Q_f$ based on an initial $Q_{f0}$ according to Equation 4. At stage 1004, dialysis system 12 sets the UF pump to the determined UF rate $Q_f$ for an active time T and measures ΔBV at the end of the active time T. At stage 1006, dialysis system 12 sets the UF pump to a minimum rate $Q_{min}$ which in some embodiments is 150 ml/hr or 10 ml/hr. The UF pump is at $Q_{min}$ for rebound time T and ΔBV is measured for the rebound time. At stage 1008, stages 1004 and 1006 are repeated to obtain an initial regression set. For example, an initial regression set may involve 3 measurement periods as previously described. The initial regression set holds ordered pairs of 3 values of cumulative ΔBV in each of the active times and 3 values of ΔBV for each of the rebound times.

At stage 1010, dialysis system 12 determines next UF rate $Q_f$ using the regression set of stage 1008. As previously described, a second order polynomial may be used to characterize how refill rate of the patient responds to successive changes in blood volume. Based on the regressed H'(UFR,t) polynomial, the expected fluid rebound at the last treatment period can be solved for, and the next UF rate $Q_f$ to reach the expected fluid rebound determined.

At stage 1012, the dialysis system sets the UF pump to the next UF rate $Q_f$ for active time T and measures ΔBV at the end of the active time T. At stage 1014, dialysis system 12 sets the UF pump to the minimum rate $Q_{min}$ for rebound time T and measures ΔBV for the rebound time. At stage 1016, the new measurements from stages 1012 and 1014 are incorporated in the regression set, and the oldest ΔBV measurements are dropped from the regression set. For example, as discussed above with respect to FIG. 9, after X1-X3 and Y1-Y3 were regressed and $Q_{f2}$ adjusted, the measurements during period P4 and D created ordered pairs (X4, Y4) which were used in the next regression while ordered pair (X1, Y1) were dropped from the next regression. At stage 1018, stages 1010 through 1016 are repeated either until a target rebound is achieved or until a predetermined treatment time is reached.

As previously outlined, there is some evidence through analysis of morbidity and death events that suggests certain ranges of fluid removal at specific times in the treatment are more effective in preserving patient health than other estimation methods. ΔBV cumulative amount targets for the active UF times can be specified to minimize stress on the patient's system while still striving to obtain the best dry-weight approximation achievable.

In an alternate fluid removal embodiment of Example 3, instead of varying the UF pump rate for fixed time intervals based on the rebound, a profile can be described where the UF pump is operated at a fixed removal level for variable lengths of time. For example, suppose that from previous experience and history with the patient, the physician designates a UF rate of 1800 ml/hr as an estimate to approach dry weight at the end of the dialysis treatment. The UF pump is kept at the same UF rate while rebounds are checked at variable intervals. In an example embodiment, the refill rebounds during fixed intervals (e.g. 5 minutes) can be measured with UF set to minimum whenever the % ΔBV reaches progressive differences of −2%. It is understood that other difference values can be used and −2% is used as an example. It is also understood that other intervals for measuring refill rebounds can be used, and the fixed 5 minute interval is used as an example.

Figure 11:
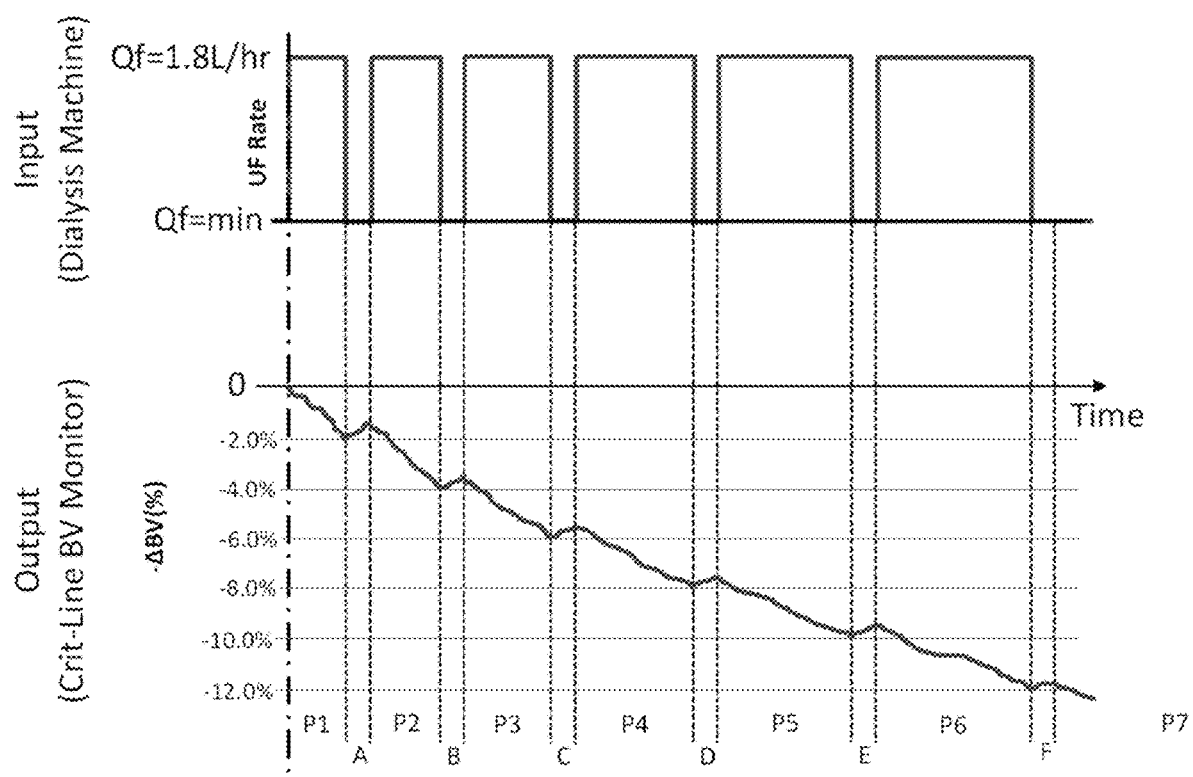
FIG. 11 illustrates an example treatment profile for a patient undergoing dialysis using a constant UF rate to evaluate time of treatment based on reaching pre-established BV waypoints.
Figure 12:
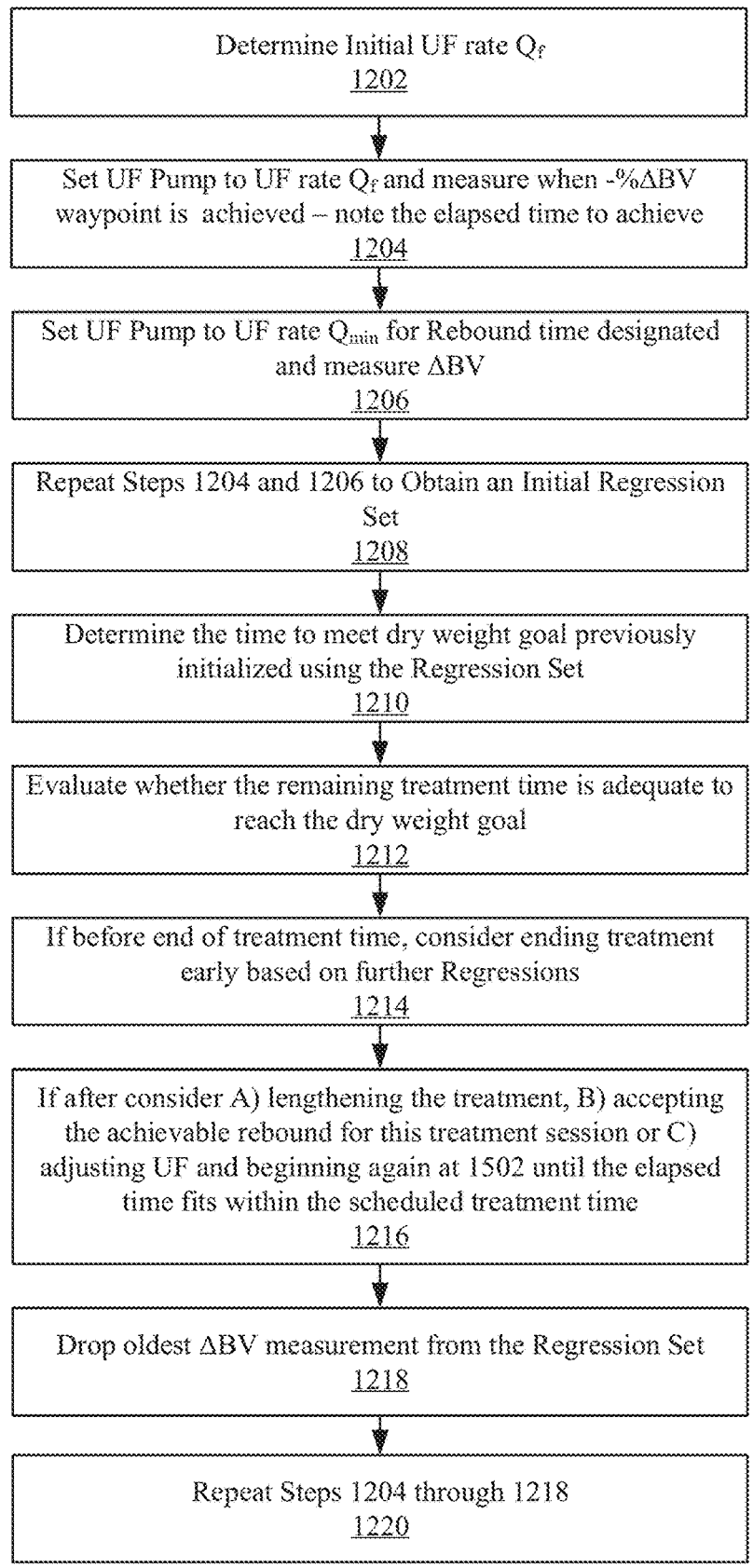
FIG. 12 is a process flowchart of a dialysis treatment using a constant UF rate according to an embodiment of the disclosure.

FIG. 11 shows a sample progression using a −2% difference as the treatment is conducted. Because the body's ability to yield fluid varies and generally drops as dialysis progresses due to changes in available excess fluid and changes in the vascular system, the time periods to meet the prescribed goals (or −2% waypoints) will usually not be constant. The sample progression of FIG. 11 will be described with the aid of the flow diagram in FIG. 12. FIG. 12 is a process flowchart of a dialysis treatment using a constant UF rate according to an embodiment of the disclosure. At stage 1202, the initial UF rate is determined, which as an example can be 1800 ml/hr as determined by the physician.

At stage 1204, dialysis system 12 sets the UF pump to the determined UF rate $Q_f$ and measures when −% ΔBV waypoint is achieved and notes elapsed time to achieve the −ΔBV waypoint. At stage 1204, FIG. 11 shows that the time required for the −% ΔBV to reach −2% is time period P1. At this point, the dialysis system 12 sets the UF pump to a minimum UF rate $Q_{min}$ for a designated rebound time and measures ΔBV during the rebound time. In an example, the rebound time may be a fixed 5 minutes. Minimum UF rate is based on dialysis system 12 architecture—rarely can minimum UF rate be zero to maintain a safe transmembrane pressure in the dialyzer filter. The rebound volume amount, A, during this time is measured, at stage 1206. The amount of fluid removed, that is, UF rate $Q_f$ multiplied by elapsed time during the UF active period for ΔBV to decrease by −2% ΔBV, is determined as the blood volume removed by dialysis. This volume is stored as X1, while the measured rebound volume A is stored as Y1. At the end of the 5 minute rebound time, the current level of ΔBV is measured and a new waypoint is established by subtracting 2% from the previous waypoint. Once the new waypoint is established, the UF pump is reactivated by the dialysis system 12 at UF rate $Q_f$ until the waypoint is reached.

When the waypoint is achieved, the UF rate is again reduced to $Q_{min}$ for a fixed duration, e.g., 5 minutes, and the refill, B, is measured. The dialysis system 12 determines the total volume removed from the patient and stores this volume as variable X2. The total volume removed is determined as the sum of X1 and UF rate $Q_f$×elapsed time the UF pump was running to move to the new waypoint. The 5 minute rebound, B, is recorded as Y2. At the end of the 5 minute rebound time, the current level of ΔBV is measured and a new waypoint is established by subtracting 2% from the previous waypoint. The UF pump is then reactivated until the new waypoint is reached. When the waypoint is achieved, the UF rate is once again reduced by dialysis system 12 to $Q_{min}$ for a fixed 5 minute interval and the refill, C, is measured. The dialysis system 12 then determines the total volume removed from the patient and stores this volume as variable X3. The total volume removed is determined as the sum of X2 and UF rate $Q_f$×elapsed time the UF pump was running to move to the new waypoint. The 5 minute rebound, C, is recorded as Y3, thus competing stage 1208, since an initial regression set including (X1, Y1); (X2, Y2); and (X3, Y3) is obtained. Three data sets are used as an example, but more than three data sets may be provided as the initial regression set.

At stage 1210, analogous to stage 1010, the dialysis system 12 determines a first solution for finding $H_1'(UFR, t)$ by regressing the ordered pairs (X1, Y1); (X2, Y2); and (X3, Y3) using numerical analysis methods to produce a second order polynomial characterizing how the refill rate of the patient is responding to successive removal periods of blood volume based on the dialysis treatment. The resulting polynomial will be of the same form as Equation 5.

In Equation 5, Y is the desired target rebound (zero being an indication of near dry weight). X is the relative percentage of fluid removal as measured on the Crit-Line® or similar device as the % ΔBV which is proportional to Time×UF rate. By setting (5) equal to zero for Y (no rebound–dry weight), X can be solved for. Dividing X by the fixed UF rate, the time required to achieve the Y target can be solved for, thus completing stage 1210.

Note that an X value (change in patient overall blood volume due to active UF) is the area found between the traces while UF is active and the zero axis. This area is a function of UF rate $Q_f$, e.g., 1,800 ml/hr, and elapsed active UF times (e.g., P1, P2, . . . Pn). Therefore, the volume dialyzed is a function of the UF rate and the time periods UF is active. In this embodiment, the UF pump rate remains fixed, and the time periods P1-Pn are considered variable to achieve the overall −% ΔBV goal established at the beginning of the treatment.

Based on the regressed $H_1'(UFR, t)$ polynomial derived with (X1, Y1); (X2, Y2); and (X3, Y3), the expected fluid rebound can be projected for the end of the final treatment time. The fluid rebound is a measure of how much fluid is left in the body above the normal blood volume level as if the patient had kidney function. The rebound amount is a function of how much total fluid has been removed from the body under the dialysis process and how the fluid dynamics of the patient react to it as if the body were a black box. Therefore, the regressed function $H_1'(UFR, t)$ relates the rebound caused by vascular re-filling to the amount of fluid removed by the dialysis treatment to the point in time these measurements are made.

If the rebound level is less than zero, then clinical intervention may be required and is not the normal expectation. If the rebound is greater than zero (the dry-weight target) then the regressed equation is set equal to zero and the time for the end of treatment to reach a zero rebound (dry-weight target) is calculated based on the fixed UF rate, at stage 1212. If the time is less than the normal designated treatment time for the patient (typically 3 hours in the USA), the patient will appear to be finishing dialysis early that day, stage 1214. If the time to reach the zero rebound point is projected to be longer than the remaining treatment time, then the target can be held over to the next dialysis treatment and the process repeated but with a higher UF rate, at stage 1216. Stage 1216 indicates that the treatment length may be increased as option (A), a sub-optimal rebound may be accepted as option (B), or the UF rate for the next treatment may be adjusted based on the regression set such that the time to reach zero rebound point is within the scheduled treatment time.

After each waypoint is reached, the same data collection regime is followed for a 2% decrease in BV (or other designated waypoint difference value). The next data will include X4 for the blood volume removal percentage and Y4 for the associated 5 minute period rebound. At stage 1218, the first ordered pairs of X1, Y1 are dropped, and the regression is repeated using the ordered pairs of data (X2, Y2); (X3, Y3); and (X4, Y4). Note that (X4, Y4) is obtained after repeating stages 1204 and 1206 as indicated in stage 1220. In stage 1220, since a regression set is already obtained, the repetition prescribed at stage 1208 is not performed. Stage 1220 thus involves repeating stages 1204, 1206, 1210, 1212, 1214, 1216 and 1218. As these regressions progress, the change in patient fluid dynamics are accounted for, and setting the Y value to zero in Equation 5 knowing the fixed UF rate allows for a new projection of the time required to reach a zero rebound (dry weight). The 5 minute rebound time is used as an example and other rebound time values can be used as long as the rebound time values are consistent and long enough for any re-fill to be measured by the dialysis system 12.

In some embodiments, it is desirable and more comfortable to the patient to leave limited amount of fluid over the projected dry weight on the body. Those skilled in the art and experienced with real treatments in various dialysis scenarios can define a refill rate that could be substituted for zero in solving the regression equations. This substitution for zero can apply to fixed time and/or fixed UF rate embodiments.

FIG. 13 is a detailed flowchart of a dialysis treatment following principles of Example 1 according to an embodiment of the disclosure. At stage 1302, dialysis system 12 receives an initial UF rate, a length of the dialysis treatment, a hysteresis for UF pump uncertainty, and a target ΔBV. The initial UF rate, the length of the dialysis treatment, and the target ΔBV may be determined based on previous patient treatment history and/or the patient's assessed condition by a clinician. The hysteresis for the UF pump uncertainty may be determined based on previously identified sensitivity of the UF pump.

At stage 1304, dialysis system 12 sets the UF rate to the initial UF rate, initializes a cumulative ΔBV percentage to zero, turns on the UF pump thus initiating the dialysis treatment, and saves a start time of when the UF pump was turned on. At stage 1306, dialysis system 12 periodically samples the cumulative ΔBV percentage. For example, dialysis system 12 obtains one sample of the cumulative ΔBV percentage every second.

At stage 1308, dialysis system 12 calculates, for each sample, a benchmark ΔBV percentage. In an embodiment, the benchmark ΔBV percentage can be obtained according to Equation 6.

$$\text{benchmark } \%\Delta BV = \frac{\text{Treatment Length}}{\text{Current Time} - \text{Start Time}} \times \text{target } \%\Delta BV \quad (6)$$

At stage 1310, dialysis machine 12 determines whether the dialysis treatment is complete. Dialysis treatment is complete when current time is equal to or exceeds treatment length. If dialysis treatment is complete, then dialysis machine 12 shuts off the UF pump at stage 1370, and if dialysis treatment is not complete, then dialysis machine 12 determines status of the UF pump at stage 1320. At stage 1320, based on the status of the UF pump, cumulative ΔBV percentage, benchmark ΔBV percentage, and the hysteresis for the UF pump, dialysis machine 12 either keeps the current status of the UF pump or changes the status of the UF pump.

At stage 1320, if the UF pump is off, then at stage 1330, dialysis machine 12 determines whether the cumulative ΔBV percentage is greater than or equal to a sum of the benchmark ΔBV percentage and the hysteresis. If the cumulative ΔBV is greater than or equal to the sum of the benchmark ΔBV percentage and the hysteresis, then at stage 1350, dialysis machine 12 turns on the UF pump before continuing to sample the cumulative ΔBV percentage at stage 1306; otherwise, dialysis machine 12 continues sampling the cumulative ΔBV percentage at stage 1306 while keeping the UF pump off.

At stage 1320, if the UF pump is on, then at stage 1340, dialysis machine 12 determines whether the cumulative ΔBV percentage is less than or equal to a difference between the benchmark ΔBV percentage and the hysteresis. If the cumulative ΔBV is less than or equal to the difference of the benchmark ΔBV percentage and the hysteresis, then at stage 1360, dialysis machine 12 turns off the UF pump before continuing to sample the cumulative ΔBV percentage at stage 1306; otherwise, dialysis machine 12 continues sampling the cumulative ΔBV percentage at stage 1306 while keeping the UF pump on.

Figure 14:
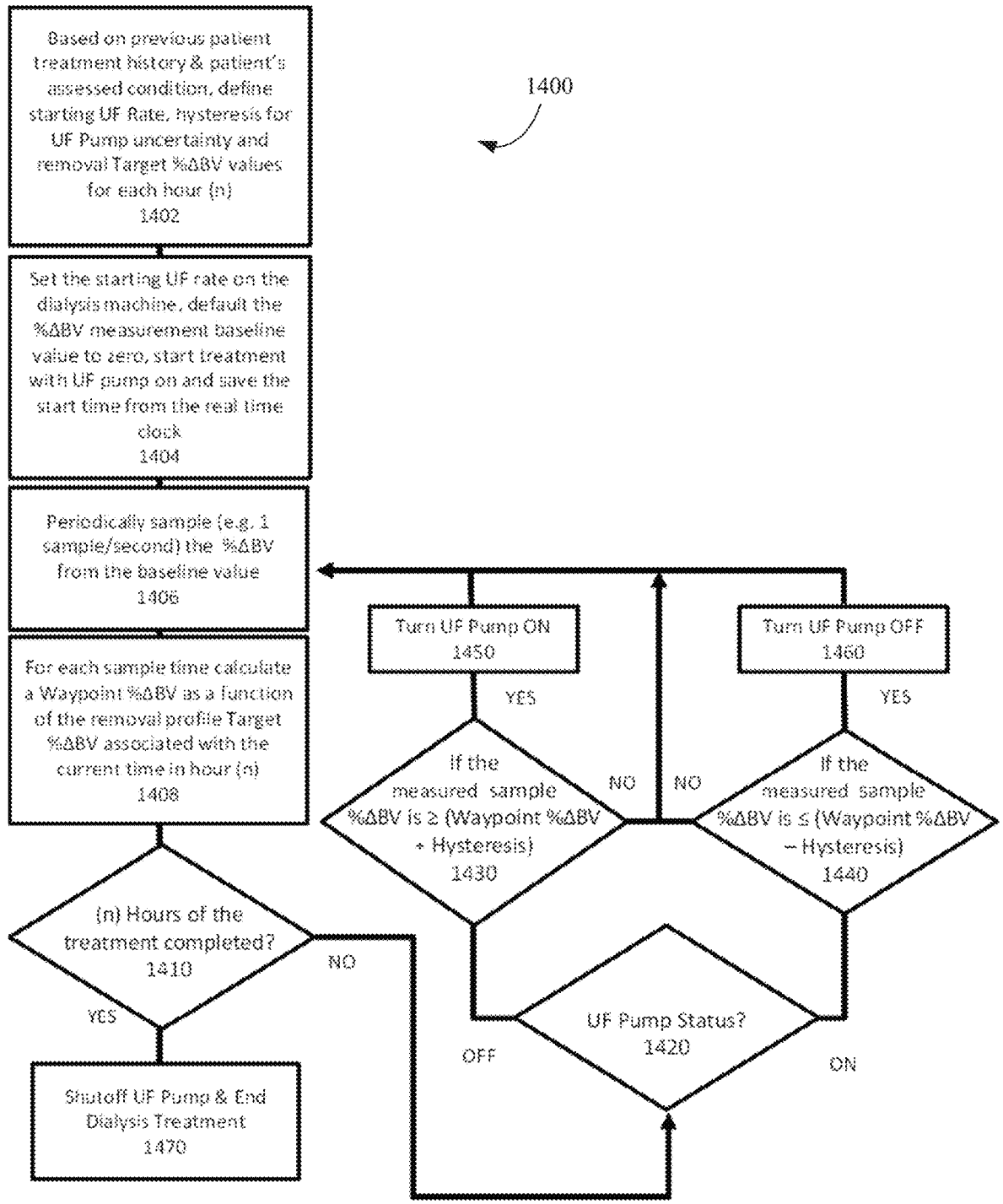
FIG. 14 is a process flowchart of a dialysis treatment according to an embodiment of the disclosure.

FIG. 14 is a flowchart of a dialysis treatment following principles of Example 2 according to an embodiment of the disclosure. At stage 1402, dialysis system 12 receives a starting UF rate, a hysteresis for UF pump uncertainty, and a target ΔBV percentage values for each hour n of dialysis treatment. At stage 1404, dialysis system 12 sets the UF rate to the starting UF rate, initializes a baseline ΔBV percentage to zero, turns on the UF pump thus initiating the dialysis treatment, and saves a start time of when the UF pump was turned on.

At stage 1406, dialysis system 12 periodically measures sampled ΔBV percentage. Sampled ΔBV percentage is cumulative ΔBV percentage during hour n minus the baseline ΔBV percentage during hour n. For example, in FIG. 5, during hour 1, dialysis system 12 obtains one sample of the cumulative ΔBV percentage every second and subtracts the baseline ΔBV percentage for hour 1. In FIG. 5, the baseline ΔBV percentage for hour 1 is 0, for hour 2 is −7%, and for hour 3 is −10%. In some embodiments, baseline ΔBV percentage is the cumulative ΔBV percentage at the beginning of the hour.

At stage 1408, dialysis system 12 calculates a waypoint ΔBV percentage as a function of a removal profile target ΔBV percentage associated with the current time in hour n. For example, FIG. 5 shows removal profile targets of −7%, −3%, and −2% associated with hours 1, 2, and 3, respectively to obtain a total removal of −12% over the three hour period. During each hour in FIG. 5, a waypoint ΔBV percentage is calculated for each sample as a function of target ΔBV percentage associated with the hour. The waypoint ΔBV percentage can be calculated according to Equation 7:

$$\text{Waypoint } \%\Delta BV = \frac{n}{\text{Current Time} - \text{Start Time}} \times \text{target } \%\Delta BV(n) \quad (7)$$

where n is the hour of the treatment and target % ΔBV(n) is the target for hour n.

At stage 1410, dialysis machine 12 determines whether the dialysis treatment is complete. Dialysis treatment is complete when n hours of the treatment is completed. Based on the duration of treatment, if dialysis machine 12 determines that duration is greater than or equal to n hours, then the UF pump is shut off and dialysis treatment is ended at stage 1470. At stage 1410, if dialysis treatment is not completed, then dialysis machine 12 determines status of the UF pump at stage 1420. At stage 1420, based on the status of the UF pump, sampled ΔBV percentage, waypoint ΔBV percentage, and the hysteresis for the UF pump, dialysis machine 12 either keeps the current status of the UF pump or changes the status of the UF pump.

At stage 1420, if the UF pump is off, then at stage 1430, dialysis machine 12 determines whether the sampled ΔBV percentage is greater than or equal to a sum of the waypoint ΔBV percentage and the hysteresis. If the sampled ΔBV is greater than or equal to the sum of the waypoint ΔBV percentage and the hysteresis, then at stage 1450, dialysis machine 12 turns on the UF pump before continuing to measure the next sampled ΔBV percentage at stage 1406; otherwise, dialysis machine 12 continues measuring the sampled ΔBV percentage at stage 1406 while keeping the UF pump off.

At stage 1420, if the UF pump is on, then at stage 1440, dialysis machine 12 determines whether the sampled ΔBV percentage is less than or equal to a difference between the waypoint ΔBV percentage and the hysteresis. If the sampled ΔBV is less than or equal to the difference of the benchmark ΔBV percentage and the hysteresis, then at stage 1460, dialysis machine 12 turns off the UF pump before continuing to measure the next sampled ΔBV percentage at stage 1406;

otherwise, dialysis machine 12 continues measuring the sampled ΔBV percentage at stage 1406 while keeping the UF pump on.

ΔBV percentage in embodiments of the disclosure are changes with respect to fluid removal during dialysis. As such, certain embodiments discuss ΔBV as an absolute value and others provide a negative sign indicating that as treatment is progressing and the UF pump is on, change in blood volume of the patient is decreasing. The use of a negative value or an absolute value does not limit the scope of the disclosure.

Embodiments or implementations discussed herein may be combined with each other in appropriate combinations in connection with the system described herein. Additionally, in some instances, the order of steps in the flow diagrams, flowcharts and/or described flow processing may be modified, where appropriate. The system may further include a display or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication, and may include use of one or more transmitter or receiver components that securely transmit information via a network, such as via the Internet, and/or using local area networks (LANs), such as WiFi, Bluetooth or other short range transmission protocols, or wide area networks (WANs), such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

Accordingly, in some embodiments, a dialysis system is described. In some embodiments, the dialysis system is a closed-loop dialysis system. In some embodiments, and using elements and techniques according to that further discussed elsewhere herein, a dialysis system comprises an ultrafiltration rate component that determines an initial ultrafiltration rate, a measurement sensor that measures total change in blood volume, and an implementing component. In certain embodiments, the sensors and components discussed herein may include one or more of software, hardware, a combination of software and hardware and other computer-implemented or computer-controlled modules or devices.

In some embodiments, a dialysis system comprises a dialysis machine and a processor performing various software-controlled steps, such as one or more of the software-controlled steps discussed elsewhere herein. In certain embodiments, the software-controlled steps performed by the processor include storing pairwise values in one or more non-transitory computer readable media and using the stored pairwise values to determine an ultrafiltration rate. In other embodiments, the stored pairwise values are used by the processor to determine a time that a patient will achieve dry weight. In certain embodiments, the software-controlled steps performed by the processor include using the stored pairwise values to obtain a polynomial.

In some embodiments, the dialysis machine receives pump control signals via the processor. In certain embodiments, the pump control signals provided via the processor regulate whether an ultrafiltration pump in the dialysis machine is turned ON or turned OFF. In certain embodiments, the pump control signals further determine a pump rate for the ultrafiltration pump.

In some embodiments, the processor receives initial settings from a user interface, the initial settings including one or more of a dialysis treatment period, an active time for the ultrafiltration pump, a rebound time for the ultrafiltration pump, and a dialysis treatment profile. Initial settings can be stored in computer readable media as discussed herein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for performing closed loop dialysis treatment comprising:
   (a) determining an ultrafiltration rate;
   (b) setting an ultrafiltration pump to the determined ultrafiltration rate for an active duration;
   (c) measuring a total change in blood volume;
   (d) setting the ultrafiltration pump to a minimum pump rate for a rebound duration;
   (e) measuring a rebound change in blood volume;
   repeating steps (b)-(e) a first number of times to obtain a regression set, the regression set comprising a number of pairwise values, wherein each pairwise value is a measurement of the total change in blood volume and a measurement of the rebound change in blood volume;
   (f) updating the ultrafiltration rate using the regression set;
   (g) updating the regression set by repeating steps (b)-(e); and
   repeating steps (f) and (g) a second number of times, wherein a total duration of one plus the first number of times and one plus the second number of times is a treatment period.

2. The method according to claim 1, wherein repeating steps (b)-(e) the first number of times to obtain the regression set comprises:
   repeating steps (b)-(e) two times to obtain the regression set.

3. The method according to claim 1, wherein step (a) comprises determining the ultrafiltration rate from:
   a total fluid volume to be removed during the dialysis treatment;
   a past patient treatment tolerance;
   lab measurements;
   physical examinations; and/or
   weight at time of presenting for dialysis.

4. The method according to claim 1, wherein step (a) comprises determining that the ultrafiltration rate is an initial ultrafiltration rate multiplied by a factor based on an amount of time that the ultrafiltration is expected to be at the minimum pump rate during the treatment period.

5. The method according to claim 1, wherein the treatment period is 3 hours, the rebound duration is 5 minutes, and the active duration is 15 minutes.

6. The method according to claim 1, wherein step (f) comprises:
   regressing the pairwise values in the regression set to obtain a polynomial;
   solving for an expected rebound change in blood volume at the end of the treatment period based on the polynomial; and
   updating the ultrafiltration rate based on the expected rebound change in blood volume at the end of the treatment period.

7. The method according to claim 1, wherein step (g) further comprises updating the regression set by dropping a least recent pairwise value from the regression set.

8. A method for performing closed loop dialysis treatment comprising:
   (a) determining an ultrafiltration rate;
   (b) setting an ultrafiltration pump to the determined ultrafiltration rate for an active duration;
   (c) measuring a total change in blood volume during the active duration to determine when a blood volume waypoint is met;
   (d) setting the ultrafiltration pump to a minimum pump rate for a rebound duration;
   (e) measuring a rebound change in blood volume for the rebound duration;
   (f) updating the blood volume waypoint;
   repeating steps (b)-(f) a first number of times to obtain a regression set, the regression set comprising a number of pairwise values, wherein each pairwise value is a measurement of the total change in blood volume and a measurement of the rebound change in blood volume;
   (g) determining a dry weight time to meet a dry weight goal using the regression set; and
   (h) determining whether the treatment period is adequate to reaching the dry weight goal.

9. The method according to claim 8, further comprising:
   based on the treatment period being adequate to reaching the dry weight goal, dropping a least recent pairwise value in the regression set;
   updating the regression set by repeating steps (b)-(f); and
   repeating steps (g) and (h).

10. The method according to claim 8, further comprising:
    based on the treatment period not being adequate to reaching the dry weight goal, stopping the closed loop dialysis treatment.

11. The method according to claim 8, further comprising:
    based on the treatment period not being adequate to reaching the dry weight goal, dropping a least recent pairwise value in the regression set;
    adjusting the ultrafiltration rate;
    updating the regression set by repeating steps (b)-(f); and
    repeating steps (g) and (h).

12. The method according to claim 8, wherein determining the dry weight time to meet the dry weight goal using the regression set comprises:
    regressing the pairwise values in the regression set to obtain a polynomial;
    solving for an expected rebound change in blood volume at the end of the treatment period based on the polynomial; and
    updating the dry weight time based on the expected rebound change in blood volume at the end of the treatment period.

13. The method according to claim 8, wherein the treatment period is 3 hours and the rebound duration is 5 minutes.

14. The method according to claim 8, wherein updating the blood volume waypoint comprises increasing the blood volume waypoint by a fixed percentage.

* * * * *